United States Patent
Heaven

(10) Patent No.: US 8,658,355 B2
(45) Date of Patent: Feb. 25, 2014

(54) GENERAL MASS SPECTROMETRY ASSAY USING CONTINUOUSLY ELUTING CO-FRACTIONATING REPORTERS OF MASS SPECTROMETRY DETECTION EFFICIENCY

(75) Inventor: Michael R Heaven, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/698,725

(22) PCT Filed: May 17, 2011

(86) PCT No.: PCT/US2011/036862
§ 371 (c)(1),
(2), (4) Date: Nov. 19, 2012

(87) PCT Pub. No.: WO2011/146521
PCT Pub. Date: Nov. 24, 2011

(65) Prior Publication Data
US 2013/0068943 A1      Mar. 21, 2013

Related U.S. Application Data

(60) Provisional application No. 61/345,312, filed on May 17, 2010, provisional application No. 61/416,561, filed on Nov. 23, 2010.

(51) Int. Cl.
*C12Q 1/70* (2006.01)
*G01N 31/00* (2006.01)

(52) U.S. Cl.
USPC .................................. 435/5; 435/4; 250/282

(58) Field of Classification Search
USPC ................ 250/282; 436/173, 86, 518, 6.18, 5
See application file for complete search history.

(56) References Cited

U.S. PATENT DOCUMENTS 6,864,098 B2    3/2005   Ammon
7,158,903 B2    1/2007   Kushnir
(Continued)

FOREIGN PATENT DOCUMENTS

AU    2003304434    3/2005
DE    10145904      4/2003
(Continued)

OTHER PUBLICATIONS

Geiger, Tamar, et al. "Super-SILAC mix for quantitative proteomics of human tumor tissue" Nature Methods; vol. 7, No. 5; May 2010; pp. 383-387.

(Continued)

*Primary Examiner* — Nikita Wells
*Assistant Examiner* — Johnnie L Smith
(74) *Attorney, Agent, or Firm* — Thomas G. Peterson; Bradley Arant Boult Cummings LLP

(57) ABSTRACT

The invention provides general methods for quantifying any conceivable compound including small organic molecules and biological molecules in mass spectrometric measurements. The methods include the use of chemical or biological reporters such as artificial polypeptides containing proteolytic cleavage sites, which provide proteolytic reporter peptides for standardization of mass spectrometric detection efficiency. In addition to mass spectrometry standardization between different samples, the artificial polypeptides also standardize sample preparation amongst different samples undergoing mass spectrometric analysis when using electrophoresis separation prior to mass spectrometric analysis. Methods of the present invention also include methods for designing artificial polypeptides with peak to peak continuous liquid chromatography elution profiles spanning the complete or partial analyte elution profile for organic and biological molecules. Also included are the artificial polypeptides predigested with protease, which is compatible for use in experiments with native PAGE, in-solution proteolytic digestion of polypeptides, and small organic molecules undergoing fractionation separation followed by mass spectrometric evaluation.

31 Claims, 25 Drawing Sheets

(56) References Cited

U.S. PATENT DOCUMENTS

| | | | |
|---|---|---|---|
| 7,451,052 B2 | 11/2008 | Wang | |
| 2003/0066802 A1 | 4/2003 | Jastorff et al. | |
| 2004/0153249 A1 | 8/2004 | Zhang et al. | |
| 2005/0069916 A1* | 3/2005 | Chait et al. | 435/6 |
| 2007/0207555 A1* | 9/2007 | Guerra et al. | 436/518 |
| 2007/0218560 A1 | 9/2007 | Pillai | |
| 2008/0026480 A1* | 1/2008 | Guerra | 436/86 |
| 2008/0101989 A1 | 5/2008 | Pappin | |
| 2008/0203284 A1 | 8/2008 | Grothe | |
| 2008/0241955 A1* | 10/2008 | Purkayastha et al. | 436/173 |
| 2009/0002703 A1* | 1/2009 | Parman | 356/326 |
| 2009/0101809 A1 | 4/2009 | Wilbert | |
| 2009/0132171 A1 | 5/2009 | Goto | |
| 2010/0167267 A1* | 7/2010 | Schulzknappe et al. | 435/5 |
| 2011/0151494 A1 | 6/2011 | Koomen | |
| 2011/0202287 A1 | 8/2011 | Ivosev | |
| 2011/0282587 A1* | 11/2011 | Jones et al. | 702/19 |

FOREIGN PATENT DOCUMENTS

| | | |
|---|---|---|
| GB | 2382429 | 11/2005 |
| JP | 2008-065566 | 1/2009 |
| JP | 2009-158106 | 7/2009 |
| WO | 2005017646 | 2/2005 |
| WO | 2008110581 | 9/2008 |

OTHER PUBLICATIONS

Cavaliere, Chiara, et al. "Absolute quantification of cardiac troponin T by means of liquid chromatography/triple quadrupole tandem mass spectrometry" Rapid Commun. Mass Spectrom. 2008; 22: 1159-1167.

Nho, Ji Myong "International Search Report" Feb. 23, 2012, p. 1-3.

Frohlich et al. "Proteome research based on modern liquid chromatography—tandem mass spectrometry: separation, identification and quantification" Journal of Neural Transmission; Jul. 13, 2006, vol. 113, No. 8, pp. 973-994.

Niessen "Progress in liquid chromatography—mass spectrometry instrumentation and its impact on high-throughput screening" Jouranl of Chromatography A; Jun. 2003, vol. 1000, Issues1-2, pp. 413-436.

\* cited by examiner

FIG. 1. Illustration of an application of artificial proteins in a shotgun proteomics experiment.

FIG. 2. Schematic of applying the chemical or biological reporter set immediately prior to mass spectrometry analysis.

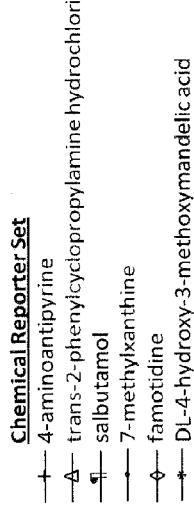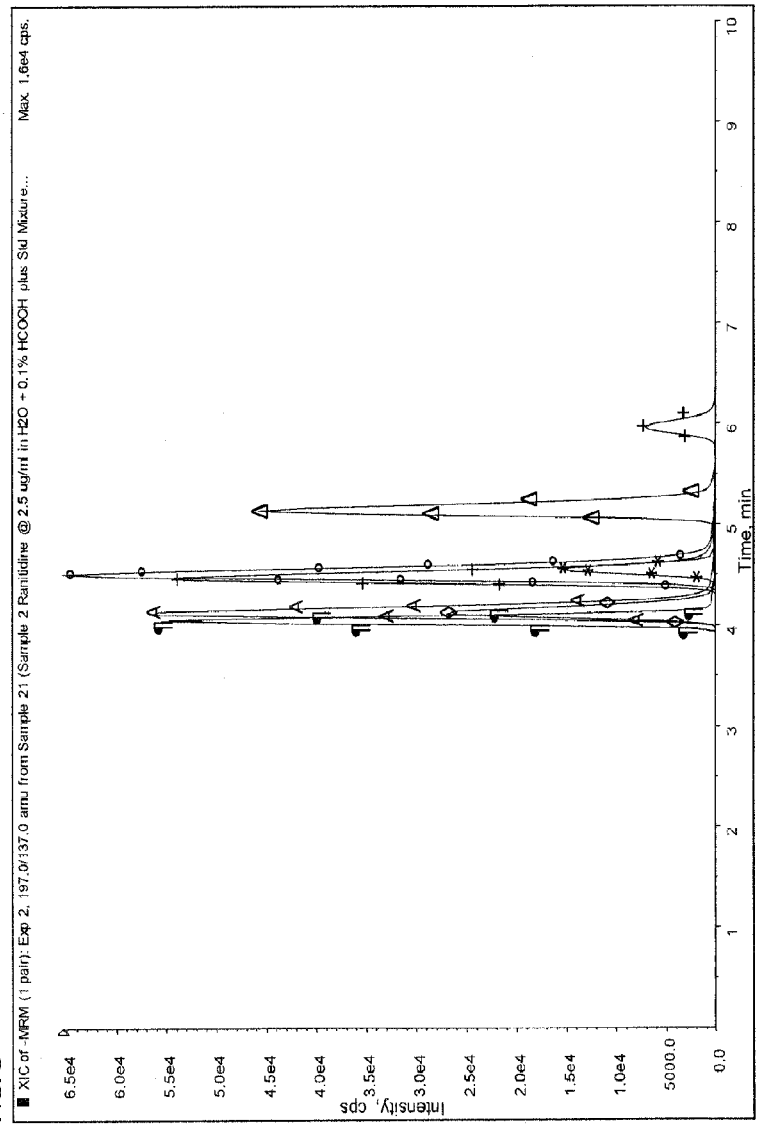
FIG. 3

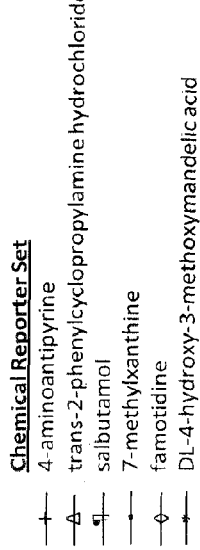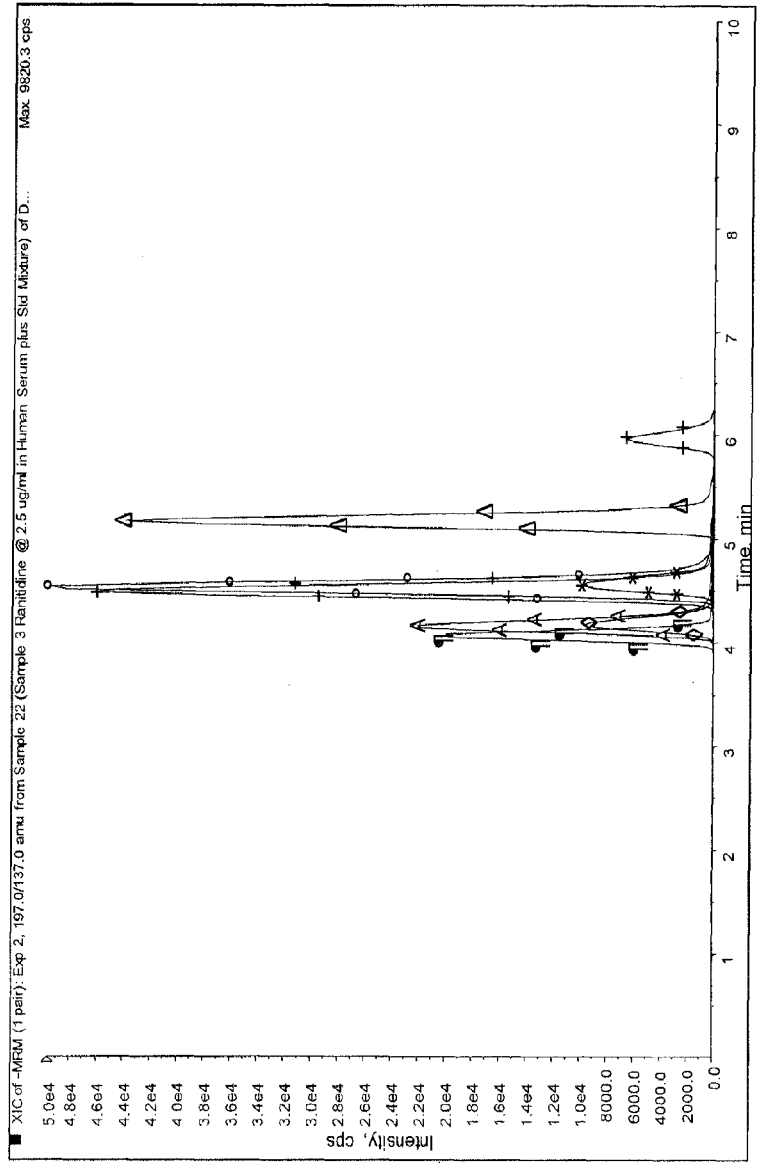
FIG. 4

FIG. 7

| Artificial Peptide Reporters | Predicted Retention Time (min) | Actual Retention Time (min) |
| --- | --- | --- |
| KPAAAAAAFR | 7.648 | 10.32 |
| KPAAAAAAALR | 7.846 | 7.76 |
| KPAGVAWR | 7.978 | 8.15 |
| KPAAAAAAAFR | 8.176 | 8.2 |
| KPAAAAAAWR | 8.374 | not observed |
| KPAAAAAAAWR | 8.506 | 8.39 |
| KPAIIINR | 8.638 | 8.26 |
| KPAIIIAR | 8.77 | 8.48 |
| KPAAAAAAAAAFR | 8.902 | 9.36 |
| KPAAAAAAAAWR | 9.1 | 8.97 |
| KPAAAAAAAAAWR | 9.298 | 13.4 |
| KPAVAIFR | 9.364 | 9.47 |
| KPAAAAAAAAAAWR | 9.562 | 9.94 |
| KPAGVFVVR | 9.76 | 9.25 |
| KPAAAAAAAAAAAWR | 9.892 | 10.3 |
| KPAIIIVR | 10.156 | 9.19 |
| KPAIIIHR | 10.42 | 8.78 |
| KPAGVAWVAVR | 10.618 | 10.24 |
| KPAIIIGR | 10.75 | 10.13 |
| KPAIIIIR | 10.948 | 9.83 |

FIG. 8

CATATGGAAGAAGAACGTAAACCGGCGGCGGCGGCTGCGGCTTTCCGTGAAGAA
GAACGTAAACCGGCGGCGGCGGCGGCGGCACTGCGTGACGAAGATCGTAA
ACCGGCAGGTGTCGCATGGCGTGATGACGATCGCAAGCCTGCGGCGGCGGCGGC
GGCGGCATTTCGTGACGATGAACGCAAGCCCGCGGCGGCGGCGGCGGCATGGCG
TGAAGATGAACGCAAGCCAGCGGCGGCGGCGGCGGCGGCATGGAGAGAAGACG
ATCGCAAACCGGCGATTATCATTAACCGTGAAGAAGAACGCAAACCGGCGATCA
TTATCGCCCGTGAAGATGACCGCAAGCCGGCGGCGGCGGCGGCGGCGGCGGCGG
CATTCCGTGAAGCGGATGACCGCAAACCTGCGGCGGCGGCGGCGGCGGCGGCAT
GGAGGGAAGATGAACGCAAACCCGCGGCGGCGGCGGCGGCGGCGGCGGCATGG
AGGGACGATGACCGCAAACCGGCCGTGGCAATCTTTCGTGATGATGACCGCAAA
CCAGCGGCGGCGGCGGCGGCGGCGGCGGCGGCATGGAGGGATGAAGATCGCAA
ACCGGCGGGCGTTTTCGTGGTTCGTGACGAAGACCGTAAGCCTGCGGCGGCGGC
GGCGGCGGCGGCGGCGGCATGGAGGGAAGAAGAATGCCGTAAACCGGCCA
TTATCATTGTTCGTGAAGATGAACGCAAACCGGCCATCATTATCATTCATCGCGA
AGAAGAACGCAAGCCTGCAGGTGTCGCATGGGTCGCAGTGCGTGATGAAGATCG
CAAACCGGCGATTATCATCATTGGTCGTGAAGAACGCAAACCGGCTATTATTATC
ATCCGTGTTCTCGAGCACCACCACCACCACCAC

Restriction enzyme site
6xHIS tag from pET23B+ vector

FIG. 9

Protein produced:

MEEERKPAAAAAAFREEERKPAAAAAAALRDEDRKPAGVAWRDDDRKPAAAAAA
AFRDDERKPAAAAAAWREDERKPAAAAAAAWREDDRKPAIIINREEERKPAIIIARE
DDRKPAAAAAAAAFREADDRKPAAAAAAAAWREDERKPAAAAAAAAAWRDDD
RKPAVAIFRDDDRKPAAAAAAAAAAWRDEDRKPAGVFVVRDEDRKPAAAAAAAA
AAAWREEECRKPAIIIVREDERKPAIIIIHREEERKPAGVAWVAVRDEDRKPAIIIIGRE
ERKPAIIIIRVLEHHHHHH

Acidic Linker Sequences

SCHEME 1

SCHEME 2

SCHEME 3

SCHEME 4

GENERAL MASS SPECTROMETRY ASSAY USING CONTINUOUSLY ELUTING CO-FRACTIONATING REPORTERS OF MASS SPECTROMETRY DETECTION EFFICIENCY

CROSS-REFERENCE TO RELATED APPLICATIONS

This application is a national stage under 35 U.S.C. §371 of International Application PCT/US11/36862, filed on May 17, 2011, and which is currently pending international Application PCT/US11/36862 is entitled under U.S.C. §119(e) to the benefit of the filing date of provisional U.S. Patent Application 61/345,312, filed on May 17, 2010, which is currently expired. International Application PCT/US11/36862 is entitled under 35 U.S.C. §119(e) to the benefit of the filing date of provisional U.S. Patent Application 61/416,561, filed on Nov. 23, 2010, which is currently expired. The contents of International Application PCT/US11/36862 are incorporated herein by reference in their entirety.

FIELD OF THE INVENTION

The present invention relates broadly to the field of mass spectrometry. The present invention relates more specifically to the quantification of analytes, specifically to mass spectrometric quantitative analysis of analytes (including proteins, peptides, small molecule chemicals, and other organic or inorganic compounds). The present invention further provides methods of designing and producing chemical and biological reporter sets that are useful in determining mass spectrometry detection efficiency.

BACKGROUND OF THE INVENTION

Mass spectrometry (MS) is an excellent technique for quantifying the amount of known and unknown substances in complex mixtures. Although, MS does have issues that can adversely affect the ability to assay or measure chemical and biological analytes. One problematic issue is ion suppression or enhancement in electrospray ionization (ESI), atmospheric pressure chemical ionization (APCI), and matrix assisted laser desorption ionization (MALDI) that are caused by non-volatile compounds including salts, ion-pairing agents, endogenous compounds, and co-eluting compounds present in samples being evaluated by mass spectrometry. These ion suppressing or enhancing factors, referred to as sample matrix, cause changes in the efficiency of droplet formation or evaporation during the ionization process and ultimately result in an altered amount of charged analytes that reach the detector of the mass spectrometer. To illustrate this point, T. M. Annesley showed a signal response curve for caffeine in the absence and presence of serum extracts fractionated by high-pressure liquid chromatography (HPLC) coupled online to a mass spectrometer that showed a reduction in the signal for caffeine in the serum samples of 90% compared to caffeine reference solutions of equal concentration (Annesley, T M, et al *Clin Chem*, 2003; 49: 1041-1044). To address ion suppression or enhancement in liquid chromatography coupled to mass spectrometric assays internal standards have been used including stable isotopes of the compounds of interest or a compound that co-elutes with the compound of interest whereby the ion suppression or enhancement for both compounds is identical (Kitamura, R, et al *J Chromatogra B Biomed Sci Appl*, 2001; 754: 113-119), in the case of using a co-eluting compound to quantify the compound of interest, a single compound is used as the standard based on experimental knowledge of the retention characteristics.

Another method commonly used to account for matrix effects is the standard addition method (SAM), (Saxberg, B, et al *Anal Chem*, 1979; 51: 1031-1038). The SAM method works by measuring the analyte of interest in a sample with and without spiking in known amounts of the analyte. This generates a standard curve which can be extrapolated to determine the original analyte concentration. Despite SAM's widespread use for targeted measurements of specific compounds, it cannot be easily applied to proteomics or high-throughput experiments because investigators often lack a priori knowledge of what they wish to measure, purchasing standards for all the peptides of interest is prohibitively expensive, or the requirement of doing multiple measurements using the SAM is too costly.

AQUA peptides are isotopically labeled protein or peptide standards made specifically to quantitate a targeted protein or proteins of interest (Keshishian, H, et al *Mol Cell Proteomics*, 2007; 6: 2212-2229). AQUA peptides contain an isotopic mass altering atom(s) within a peptide that is diagnostic for a specific targeted protein. The AQUA peptide behaves chemically identical to the unlabeled peptide in biological samples and elutes chromatographically from reverse phase chromatographic separations at an identical retention time as the peptide from the biological sample. The AQUA peptide and the biological peptide can be differentiated by the mass spectrometer due to their mass difference. The concentration of AQUA peptide or protein is known and allows for the determination of the levels of proteins or peptides in a sample. The drawbacks to AQUA peptides include the necessity of having to purchase a separate AQUA peptide(s) for each protein to be measured from a biological sample, in some cases without experimental knowledge of the specific peptides mass spectrometry observability including limit of detection and limit of quantitation values.

A proteomics methodology referred to as QconCAT, or QCAT proteins, consist of concatenated tryptic peptides present in proteins that are being quantitatively measured in biological samples (Beynon, R, et al *Nat Methods*, 2005; 2; 587-589; Pratt, J M, et al *Nat Protoc*, 2006; 1: 1029-1043). QCAT proteins are designed to encode a set of peptides sequences that when subjected to endoproteinase cleavage are diagnostic for measuring the abundance of a targeted set of proteins in experimental samples. The gene encoding QCAT proteins are inserted into an expression vector and transformed into coli in minimal media containing $^{15}NH_4Cl$ as the nitrogen source. The amounts of target proteins in samples are determined by introducing a known amount of the isotopically labeled QCAT protein into the biological samples and co-digesting with an appropriate endopeptidase and comparing the ratios of the unlabeled biological peptides to the isotopically labeled QCAT peptides by mass spectrometry. Two major shortcomings of this approach are the need to develop a QCAT gene for each set of proteins to be quantified, and the potential for differential proteolysis occurring to the non-native form of the QCAT peptides as compared to the native peptides within their respective natural proteins.

QCAL1 artificial proteins (quantitative calibration artificial proteins) have also been used thr calibrating and defining instrument conditions (Eyers, C E, et al *J Am Soc Mass Spectrom*, 2008; 19: 1275-1280). The QCAL1 artificial protein was constructed using the same methodology as the QCAT proteins and consists of 22 tryptic peptide sequences designed to assess and optimize mass spectrometry resolution, mass calibration, linearity of signal detection, peptide separation by chromatography, and alignment of chromatograms from data collected over time from many LC/MS runs.

These artificial proteins differ from the proposed technology because of their limited elution range, which results in these proteins not being generally applicable to correct for matrix effects. More specifically, application of the QCAL1 peptides involves their use to normalize for sample analytes that share no amount of co-fractionation with the QCAL1 peptides. The main drawback to using the QCAL1 peptides is that the amount of ion suppression or enhancement can vary dramatically throughout an LC/MS run (Stahnke, H, et al *J Anal Chem,* 2009; 81: 2185-2192).

Halogenated peptides as internal standards (H-PINS) have been used when mass spectrometry analysis is preceded by liquid chromatography (Mirzaei, H, et al *J Mol Cell Prot,* 2009; 8: 1934-1946). These internal standards contain halogen atoms that have V-shaped MS1 spectra that can be used to distinguish these internal standards from peptides present in complex matrices. A group of 10 H-PINS with a broad elution range spanning an LC/MS run has been used to perform instrument calibration, estimate overall sample matrix effects, and construct chromatographic alignment maps. The shortcoming of using a limited number of peptide standards over a broad elution range to normalize for ion suppression or enhancement is that ion suppression can change rapidly during an LC separation (Stahnke, H, et al *J Anal Chem,* 2009; 81: 2185-2192).

Another method used to correct for mass spectrometry detection efficiency is postcolumn infusion of standards (Stahnke, H, et al *J Anal Chem,* 2009; 81: 2185-2192). In this procedure, a single standard is continuously added to the effluent of an LC column immediately prior to the MS ionization source. This technique permits the assessment of analyte signal suppression or enhancement by different co-eluting matrix components during an entire chromatographic separation. Infusion of standards with very different chemical properties has been found to yield similar matrix effect responses, suggesting that such surrogate standards accurately report sample matrices. Postcolumn infusion has the drawback of requiring additional pumps or gradient formers and reduced sensitivity caused by dilution of the sample with the postcolumn infusate.

Another method used to study differences in the proteomes of cells in culture is referred to as Stable Isotope Labeled Amino acids in Cell culture (SILAC) (Ong, S E, et al *Mol Cell Proteomics,* 2002; 1: 376-386). SILAC works by metabolic incorporation of an isotopically modified light or heavy amino acid into proteins. In SILAC experiments, two or more groups of cells are grown in separate culture media with different light and heavy isotopic forms of a particular amino acid. One of the cell groups may be a control and the others represent a disease state or treated groups of cells. The cell lysates from the controls and disease states are mixed and proteolytically digested to produce peptides that behave chemically identical during liquid chromatography fractionation resulting in their co-elution. The relative abundance of proteins can be determined from the relative peak intensities observed in the MS or MS/MS spectrum for different cell cultures.

Despite the utility of SILAC there exist several shortcomings. The interpretation of data is difficult because each proteolytic peptide containing heavy or light amino acids generated from different samples are combined prior to mass spectrometric analysis resulting in different molecular ions and fragment ions depending upon the number of heavy or light amino acids in each peptide (Mellwain, S, et al *Bioinformatics,* 2008; 24; 339-347). Additionally, since different isotopes are being used it is necessary to reverse label control and disease samples to ensure that the isotopes themselves do not cause protein abundance changes. For instance, the metabolic conversion of arginine to proline in eukaryotes has been documented in SILAC experiments which causes incorrect quantitation by MS (Hwang, S I, et al *Mol Cell Proteomics,* 2006; 5; 1131-1145) and because more than 50% of tryptic peptides in large data sets contain proline (Van Hoof, D, et al *Nat Methods,* 2007; 4: 677-678) this is a significant problem for quantitative proteomic measurements. The final drawback for SILAC is that the methodology cannot be used to study tissue samples from animal and human sources.

Isobaric tags for relative and absolute quantitation (iTRAQ) is an amine-specific peptide based labeling method. iTRAQ has been used to study proteomes by data-dependent (Ross, P L, et al *Mol Cell Proteomics,* 2004; 3: 1154-1169) and MRM mass spectrometry (Wolf-Yadlin, A, et al *Proc Natl Acad Sci USA,* 2007; 104: 5860-5865). There are 3 different functional areas of each iTRAQ reagent including a reactive group, balancing group, and reporter group. The iTRAQ reagents are available with 8 different reporter peptide masses whose mass differences are offset by the balancing group, so that they all have the same overall mass. Thus, up to 8 different samples can be mixed together, each tagged with a different iTRAQ reagent. Because each tag has the same overall mass, peptides common to each biological sample will be detected at the same m/z; however, on subsequent fragmentation by MS/MS, the reporter region of each iTRAQ tag is separated from the balancing group which allows determination of the sample origin abundance of each fragmented iTRAQ peptide. The relative peak intensities of the reporter mass variants of a peptide reflects the relative concentration of a particular peptide in different samples.

The drawbacks with iTRAQ include variability among samples caused by the extra steps involved in labeling with the iTRAQ reagent. Also, the sensitivity and quantitative capability with iTRAQ is greatly reduced due to the combining of samples and corresponding increase in sample complexity. This increase in sample complexity often necessitates analyzing samples multiple times by mass spectrometry and generating an exclusion list of the most abundant ions. Peptides in this list are ignored for MS/MS analysis, so that less abundant peptides are more readily sequenced. In addition, since the iTRAQ reagent reacts with primary amines, peptides not containing lysine will be labeled at the N-terminus only, whereas lysine containing peptides will be labeled at both the N-terminus and on the lysine. If the labeling reactions are incomplete, multiple products will be generated which complicate the quantitative analysis. A statistical evaluation of these iTRAQ labeling concerns has revealed that at least a 2 fold change in peptide iTRAQ ratios is required to be biologically relevant (Armenta, J M, et al *J Am Soc Mass Spectrom,* 2009; 20: 1287-1302). In addition, iTRAQ is limited in utility to mass spectrometric instruments which have the ability to measure a specific precursor ion followed by fragmentation of the precursor ion commonly referred to as MS/MS.

The ICAT reagent also isotopically tags proteins, in this case by reacting with cysteine residues (Gygi, S P, et al *Nat Biotechnol,* 1999; 17: 994-999). Samples to be compared are individually reduced, denatured, and labeled potentially providing a source of differential error prior to mixing the different samples. The ICAT labeled samples are then subjected to 1D SDS-PAGE, in-gel trypsin digestion, peptide extraction, and purification of the tagged peptides through binding of the biotin moiety incorporated into the tag to avidin. Following cleavage of the biotinavidin tag, the peptides are analyzed by LC/MS/MS. In addition to the possible variability introduced by the steps involved in labeling each individual sample, ICAT has the drawback of labeling only cysteine containing peptides which limits analysis to only a small fraction of sample peptides.

Chromatographic separation with reverse phase liquid chromatography of peptides coupled to mass spectrometry has been used in many high-throughput proteomic and targeted protein analyses. Reverse phase liquid chromatography is utilized prior to mass spectrometry to partially fractionate complex peptide mixtures, thereby increasing the number of peptides that can be identified during an LC/MS/MS experiment (de Godoy, et al *Genome Biology*, 2006; 7: R50).

In non-isotopically labeled LC-MS and LC-MS/MS proteome experiments the method of spectral counting is frequently used to obtain correlative information on quantitative differences among proteins in different samples (Washburn, M P, et al *Nat Biotechnol*, 2001; 19: 242-247). Spectral counting refers to the number of times that a particular peptide is selected for fragmentation MS/MS by the mass spectrometer, which in turn is a function of its abundance relative to other co-eluting peptides. An alternative to spectral counting in label free proteomics is comparison among different samples of the area under the MS signal peak of a particular peptide (Bondarenko, P V, et al *Anal Chem*, 2002; 74: 4741-4749). A major advantage of the label free comparative proteomic methods is that in contrast to isotope labeling methods, there are no addition steps in the sample preparation process and samples are not overwhelmed by high abundance proteins preventing the detection and quantitation of low abundance peptides by being combined prior to MS analysis. A major drawback for the label free methods are that there is no compensation for differences in the suppression or enhancement of peptides caused by the variable makeup of different sample matrix components.

SUMMARY OF THE INVENTION

The following summary of the invention is provided to facilitate an understanding of some of the innovative features unique to the present invention and is not intended to be a full description. A full appreciation of the various aspects of the invention can be obtained from taking the entire specification, claims, drawings, and abstract as a whole.

The present invention provides mass spectrometry methods for measuring the amount of analytes in different samples by utilizing reporters that co-fractionate with analytes of interest during gel electrophoresis and liquid chromatography, thereby providing standards to normalize for sample recovery and ion suppression or enhancement. One form of these reporters for proteomic studies will be individual reporter peptides or artificial proteins whose proteolysis yields a set of peptides that co-fractionate with sample analytes during liquid chromatography. Another form of these reporters for proteomic studies will be artificial proteins whose proteolysis yields a set of peptides that co-fractionate with sample analytes during liquid chromatography. In this embodiment, the artificial protein(s) co-migrate with analytes during gel electrophoresis and are recovered with the analytes from the gel. The instant invention described herein is simply added to samples being analyzed with no additional experimental procedure steps. The present invention also includes compositions and methods for designing chemical or biological reporters with peak to peak adjacent elution that span a fraction or complete LC elution range for organic and biological compounds. Methods for producing the artificial proteins using recombinant or chemical methods are also included in the disclosure.

In a first aspect, the present disclosure provides a method for characterizing an analyte in a sample In a second aspect, the present disclosure provides a method for characterizing an analyte in a sample, the methods comprising (i) combining a plurality of reporters with the sample containing the analyte to create a mixture, wherein each reporter generates a distinct reporter peak, the plurality of reporters provide a continuous set of reporter peaks during at least a fraction of the elution range of the sample and the plurality of reporters are not present in the sample or are not predicted to be created from the sample during processing of the sample; (ii) subjecting the mixture to fractionation by liquid chromatography to produce an eluate; (iii) subjecting the eluate to detection by a mass spectrometric technique to generate a mass spectrometric signal from the analyte and at least one reporter co-eluting with the analyte; and; (iv) comparing the mass spectrometric signal from analyte to the mass spectrometric signal of at least one reporter co-eluting with the analyte.

In a third aspect, the present disclosure provides a method for characterizing an analyte in a sample, the methods comprising (i) combining a plurality of chemical reporters with the sample containing the analyte to create a mixture, wherein each chemical reporter generates a distinct reporter peak, the plurality of reporters provide a continuous set of reporter peaks during at least a fraction of the elution range of the sample and the plurality of chemical reporters are not present in the sample or are not predicted to be created from the sample during processing of the sample; (ii) subjecting the mixture to fractionation by liquid chromatography to produce an eluate; (iii) subjecting the eluate to detection by a mass spectrometric technique to generate a mass spectrometric signal from the analyte and at least one chemical reporter co-eluting with the analyte; and; (iv) comparing the mass spectrometric signal from analyte to the mass spectrometric signal of at least one chemical reporter co-eluting with the analyte.

In a fourth aspect, the present disclosure provides a method for characterizing an analyte in a sample, the methods comprising (i) combining a plurality of reporter peptides with the sample containing the analyte to create a mixture, wherein each reporter peptide generates a distinct reporter peak, the plurality of reporter peptides provide a continuous set of reporter peaks during at least a fraction of the elution range of the sample and the plurality of reporter peptides are not present in the sample or are not predicted to be created from the sample during processing of the sample; (ii) subjecting the mixture to fractionation by liquid chromatography to produce an eluate; (iii) subjecting the eluate to detection by a mass spectrometric technique to generate a mass spectrometric signal from the analyte and at least one reporter peptide co-eluting with the analyte; and; (iv) comparing the mass spectrometric signal from analyte to the mass spectrometric signal of at least one reporter peptide co-eluting with the analyte.

In a particular embodiment of the third aspect the chemical reporter set comprises at least one of the following chemical classes: alcohols, esters, amines, organic acids, organic bases, ethers, sulfones, acetylenes, adamantanes, anthracenes, pyrenes, benzoquinones, anthraquinones, hydrocarbons, pyrrolidines, imides, indoles, quinolines, azulenes, carbazoles, hydroxylamines, nitriles, stilbenes, metallocenes, quaternary ammonium compounds, imidazolium compounds, pyridinium compounds, phosphonium compounds, halides, phenols, aldehydes and ketones.

In a particular embodiment of the fourth aspect, the reporter peptides may be created individually or may be generated from an artificial protein.

In the foregoing aspects, the comparing step may involve generating a ratio of the mass spectrometric signal from the analyte to the mass spectrometric signal of at least one reporter co-eluting with the analyte. In such a comparison, an increase in the ratio indicates an increased concentration of the analyte in the sample and a decrease in the ratio indicates a decreased concentration of the analyte in the sample.

In the foregoing aspects, the characterizing may be quantifying a relative amount of the analyte or quantifying an absolute amount of the analyte.

In the foregoing aspects, the methods may be used to normalize the levels of the analyte contained in different samples.

In the foregoing aspect, the plurality of reporters may be added to the sample prior to at least partial purification of the sample or may be added to the sample after purification or partial purification of the sample. In certain embodiment, the purification may be an electrophoretic purification using a gel matrix. The electrophoretic purification may be a 1-dimensional or 2-dimensional electrophoretic purification. In certain embodiment, one or more artificial proteins are subject to electrophoretic purification with the sample containin the analyte and are purified from the gel matrix with the analyte; in certain embodiment, the artificial protein and the analyte are subject to digestion in the gel matrix at the same time.

In a fifth aspect, the present disclosure provides for a reporter set for quantifying an analyte in a sample through mass spectrometry detection, In a sixth aspect, the present disclosure provides for a reporter set for quantifying an analyte in a sample through mass spectrometry detection, where the reporter set comprising a plurality of reporters, each reporter generating a distinct reporter peak wherein the plurality of reporters provide a continuous set of reporter peaks during at least a fraction of the elution range of the sample and the plurality of reporters are not present in the sample or are not predicted to be created from the sample during processing of the sample.

In a seventh aspect, the present disclosure provides for a chemical reporter set for quantifying an analyte in a sample through mass spectrometry detection, where the reporter set comprising a plurality of chemical reporters, each reporter generating a distinct reporter peak wherein the plurality of chemical reporters provide a continuous set of reporter peaks during at least a fraction of the elution range of the sample and the plurality of chemical reporters are not present in the sample or are not predicted to be created from the sample during processing of the sample.

In an eight aspect, the present disclosure provides for a biological reporter set for quantifying an analyte in a sample through mass spectrometry detection, where the reporter set comprising a plurality of reporter peptides, each reporter peptide generating a distinct reporter peak wherein the plurality of reporter peptides provide a continuous set of reporter peaks during at least a fraction of the elution range of the sample and the plurality of reporter peptides are not present in the sample or are not predicted to be created from the sample during processing of the sample.

In a particular embodiment of the seventh aspect the chemical reporter set comprises at least one of the following chemical classes: alcohols, esters, amines, organic acids, organic bases, ethers, sulfones, acetylenes, adamantanes, anthracenes, pyrones, benzoquinones, anthraquinones, hydrocarbons, pyrrolidines, imides, indoles, quinolines, azulenes, carbazoles, hydroxylamines, nitriles, stilbenes, metallocenes, quaternary ammonium compounds, imidazolium compounds, pyridinium compounds, phosphonium compounds, halides, phenols, aldehydes and ketones.

In a particular embodiment of the eighth aspect, the biological set is a plurality of reporter peptides or an artificial protein capable of generating a plurality of reporter peptides.

In the foregoing aspects, at least one amino acid in at least one of the plurality of reporter peptides may be modified. In one embodiment, the amino acid that is modified is lysine and the modification is guanidination.

In the foregoing aspects, the reporter peptides (whether produced individually or from a artificial protein) may display one or more of the following properties. In one embodiment, the reporter peptides have two charge states resulting in two mass to charge ratios for the reporter peptides to detect interference in the signals of the reporter peptides. In another embodiment, the ratio of the two charge states for the reporter peptide differs between a solution of the reporter peptides alone or in the presence of a purified standard compound, and the reporter peptides in the sample. In a further embodiment, the m/z peak for the reporter peptides is used with the greatest decrease or smallest increase in the sample relative to the solution of reporter peptides alone or in the presence of the purified standard compound. In still a further embodiment, the reporters contain an m/z fragment free from interference from peptides and peptide fragments generated by mass spectrometry fragmentation of naturally occurring peptides. In still a further embodiment, the reporter peptides are used to normalize for sample recovery, ion suppression, ion enhancement or a combination of the foregoing. In still a further embodiment, at least one of the reporter peptides co-elutes with the analyte.

In the foregoing aspects, the artificial protein comprises a plurality of reporter peptides, each reporter peptide separated by a cleavable linker, wherein on cleavage of the cleavable linker the artificial protein generates a plurality of reporter peptides. In one embodiment, the cleavable linker comprises a proteolytic digestion site, wherein on cleavage of the proteolytic digestion site the artificial protein generates the plurality of reporter peptides. In certain embodiment, the proteolytic digestion site is a target for an endoproteinase selected from the group consisting of trypsin, chymotrypsin, Lys-C, Glu-C, Asp-N proteinase K, V-8 protease, Arg-C or Pro-C. In one embodiment the endoproteinase is trypsin.

In certain embodiment, the artificial protein comprises a repeating sequence of $L_1$-[K/R—$(X)_n$—K/R-$L_2$]$_a$, wherein $L_1$ and $L_2$ are each a cleavable linker which can be the same or different and $L_2$ can vary for each repeating group, n is from 1 to 1000 and a is from 2 to 1000. In certain embodiment, the artificial protein comprises a repeating sequence of $L_1$-[R—$(X)_n$—R-$L_2$]$_a$, wherein $L_1$ and $L_2$ are each a cleavable linker which can be the same or different and $L_2$ can vary for each repeating group, n is from 1 to 1000 a is from 2 to 1000 and at least one of the repeating groups $(X)_n$ comprises a sequence K-P and the artificial protein is subject to guanidination. In the foregoing embodiment, the amino acid sequence of $L_1$, $L_2$ or both may designed to vary an isoelectric point of the artificial protein or a mass of the artificial protein.

BRIEF DESCRIPTION OF THE DRAWINGS

FIG. 3 illustrates an extracted ion chromatograms of one embodiment of a chemical reporter set of the present disclosure to measure the absolute level of ranitidine (1.25 nanogram/microliter) in formic acid.

FIG. 4 illustrates an extracted ion chromatograms of one embodiment of a chemical reporter set of the present disclosure to measure the absolute level of ranitidine (1.25 nanogram/microliter) in human plasma.

FIG. 7 shows one embodiment of an in silico set of 20 artificial reporter peptides according to the present disclosure.

FIG. 8 shows the cDNA sequence used to create the artificial reporter peptides shown in FIG. 7.

FIG. 9 shows the amino acid sequence of the product of the cDNA sequence of FIG. 8.

DETAILED DESCRIPTION OF THE PREFERRED EMBODIMENTS

Figure 1:
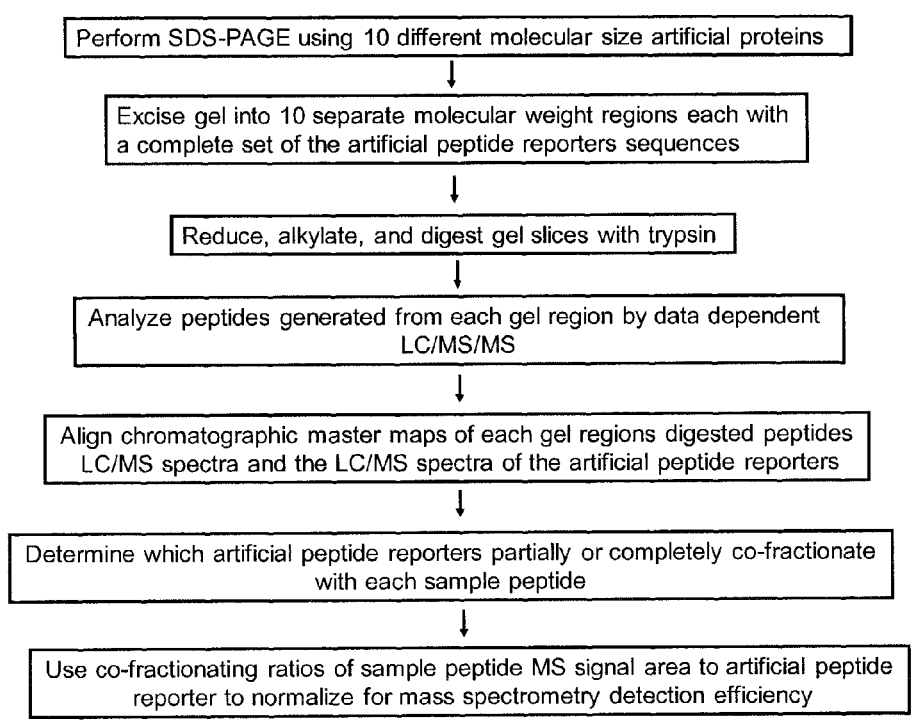
FIG. 1 depicts certain embodiments of the present invention in which the artificial proteins of various molecular weights are used to standardize for sample loss and mass spectrometry detection efficiency in shotgun proteomics experiments.
Figure 2:
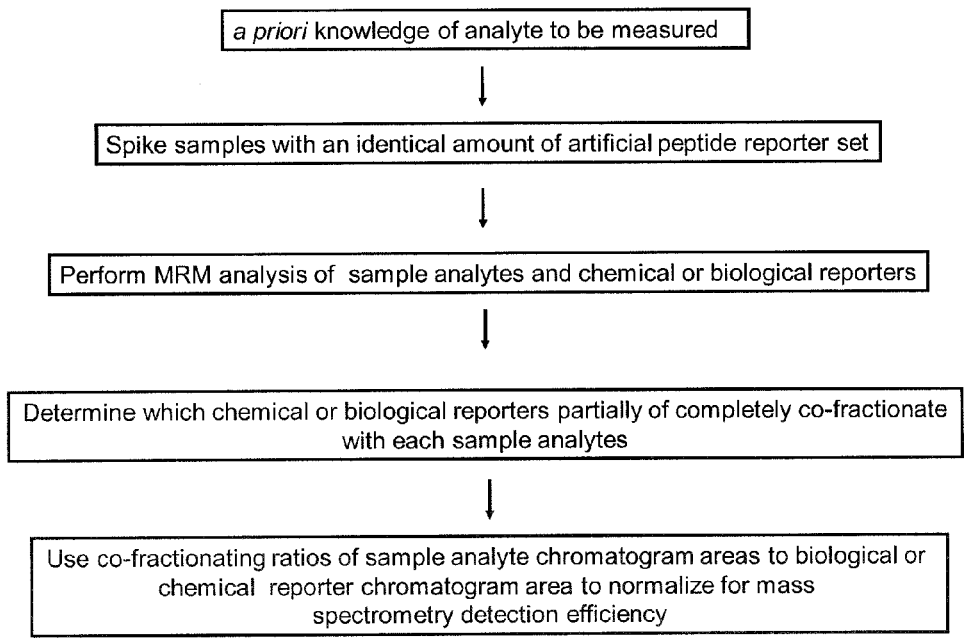
FIG. 2 depicts certain embodiments of the present invention in which the chemical or biological reporter sets are used to standardize mass spectrometry detection efficiency in different samples. An empirical example of this embodiment is also provided in examples 1 and 2.

The following description of the preferred embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The current state of the art would be facilitated by methods for absolute and relative quantification of analytes fractionated by liquid chromatography coupled to mass spectrometric analysis. Additionally, the field would be facilitated by methods providing the ability to perform absolute and relative quantification of biological samples by a method that does not involve additional experimental steps and the mixing of different experimental samples prior to mass spectrometric analysis. The field would also by methods for comparing all types of biological samples including cell culture, tissue samples, biopsies, etc. The present invention provides such tools. As such, the invention has utility for standardization and quantification of molecules by mass spectrometry.

The present invention pertains to mass spectrometry. The term "mass spectrometry", "mass spectrometric" and the abbreviations "MS" and "MS/MS" all refer to the use of mass spectrometry. However, the distinction between MS and MS/MS is that MS refers to the measurement of an m/z ratio for an analyte that is introduced into the mass spectrometer, whereas MS/MS refers to the detection of a specific m/z ratio for an analyte introduced into the instrument followed by fragmentation of the specific precursor m/z analyte and subsequent detection of fragment analyte masses. The term "MS1 spectra" refers to the detection and magnitude of m/z ratios that are introduced into the mass spectrometer over a period of time during which an analyte is eluted from a fractionation apparatus such as a high pressure liquid chromatography system. The term "chromatogram" refers to the plotting of the magnitude of a MS1 or MS/MS spectra over time as it is eluted from a fractionation apparatus connected to a mass spectrometer. The term "co-fractionating" and "co-eluting" are both synonymous with describing molecules that partially or completely share a time during which they are released from the fractionation system into a mass spectrometer.

As used herein an "analyte" is any charged molecule in a sample that is of interest to an investigator. An analyte is illustratively a protein, peptide, nucleotide, oligonucleotide, or an organic or inorganic chemical molecule.

The term "mass spectrometry" or any abbreviation thereof includes any type of ionization source including but not limited to electrospray ionization (ESI), atmospheric pressure chemical ionization (APCI), other derivatives of atmospheric pressure ionization (API), and laser irradiation such as matrix-assisted laser desorption ionization (MALD1). Suitable detection and quantitation systems illustratively include time of flight (TOF), triple quadrupole, ion traps, and other types of mass spectrometry systems known in the art. Illustratively, a Waters Q-T of Premier TOF quadrupole tandem mass spectrometer available from Waters, Corp. or an API 4000-Q trap triple quadrupole tandem mass spectrometer (Applied Biosystems, Foster City, Calif.) are each suitable for use in the instant invention, it is appreciated that other brands and types of mass spectrometers are similarly suitable.

In some applications for targeted mass spectrometric assays a triple quadrupole mass spectrometer is used in the multiple reaction monitoring mode (MRM) to detect and quantify both the inventive reporter set and desired molecule to be measured in an experimental sample. MRM has high specificity and sensitivity as a result of selecting a specific molecular ion, fragmenting said selected molecular ion, and selecting and detecting specific fragments.

In other embodiments of non-targeted, data-dependent, or discovery based mass spectrometry experiments a mass spectrometer is operated in a mode to survey the molecular ions that enter the mass spectrometer referred to as MS1 spectra followed by selection of molecular ions in the MS1 spectra and fragmentation of the selected molecular ions to gain structural information of chemicals or primary sequence determination of peptides. In data-dependent experiments the use of MS1 spectra for the reporter set and sample molecules is preferred for quantitation to obviate using MS/MS spectra which would contain fewer data points per elution cycle and have poor reproducibility due to the stochastic nature of MS/MS sequencing.

As used herein, the term "sample" is defined as a sample obtained from a biological organism, a tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial cerebrospinal fluid, blood, serum, plasma, urine, cystic fluid, lymph fluid, ascites, pleural effusion, interstitial fluid, intracellular fluid, ocular fluids, seminal fluid, mammary secretions, vitreal nasal secretions, water, air, gas, powder, soil, biological waste, feces, cell culture media, cytoplasm, cell lysate, buffers, or any other fluid or solid media. A sample is optionally a fluid containing an analyte of interest. An analyte of interest is illustratively a nucleotide, amino acid, protein, peptide, organic molecule, inorganic, molecule, or other molecule of interest (i.e., it could be any physical substance in the universe).

The term "oligonucleotide" refers to multiple nucleotides attached in the form of a single or double stranded polynucleotide that can be natural, or derived synthetically, enzymatically, and by cloning methods.

As used herein an "artificial protein" is an amino acid sequence that contains one or more cleavage sites for a protease such that cleavage of the artificial protein will yield artificial or natural peptide reporters. Illustrative examples of an endoproteinase include trypsin, chymotrypsin, Lys-C, Glu-C, Asp-N, Proteinase K, V-8 protease, Arg-C, or Pro-C. Each of these endoproteinases are available from sources known in the art, illustratively from (Sigma-Aldrich, St Louis, Mo.), or (Thermo Scientific, Rockford, N.

As used herein, the terms "engineered" and "recombinant" cells are synonymous with "host" cells and are intended to refer to a cell into which an exogenous DNA segment or gene, such as a cDNA has been introduced. Engineered cells are thus cells having a gene or genes introduced through the hand of man. Recombinant cells include those having an introduced cDNA or genomic DNA, and also include genes positioned adjacent to a promoter not naturally associated with the particular introduced gene.

The following are reasons that the present invention is advantageous over existing methods.

In comparison to QCAT proteins the present invention is superior because it is a general assay designed to permit the quantitation of potentially all mass spectrometry observable peptides of a given sample protein. In addition, since QCAT proteins must be custom produced to target a specific set of surrogate peptides representative of proteins that are desired to be quantitated, an investigator often must guess which surrogate peptides are most likely to be readily observed by the mass spectrometer. The present invention provides tools and methods for an instant approach to normalize for mass spectrometry detection efficiency in different samples.

The QCAL1 protein and H-PINS are inferior compared to the present invention because they are used to normalize sample peptides that do not co-fractionate and may thus experience an altered mass spectrometry detection efficiency.

The present invention is superior to postcolumn infusion because it simultaneously provides normalization for variations in sample preparation, LC column performance, sample injection, gradient delivery and flow rate without sample dilution.

Protein sample polyacrylamide gel procedures that involve fractionation by SDS-PAGE prior to injection of peptides into the mass spectrometer involve multiple sample preparation steps for each experimental sample, which are understood by those of ordinary skill in the art. These sample preparation steps result in potential variability between different samples when methods such as iTRAQ and AQUA peptides are used, where the iTRAQ labeling or spiking in of AQUA peptide standards does not occur until proteolytic sample peptides have been generated following SDS-PAGE. In addition, each AQUA peptide standard measures only a single surrogate peptide present in a protein, which may not be representative of the amount of that protein in a sample if post-translational modification(s) are present. The present invention provides artificial proteins that can be added prior to SOS-PAGE so that sample processing as well as mass spectrometry detection efficiency are normalized for multiple peptides from different samples.

SILAC is only applicable for use in cell culture specimens and cannot be used directly on tissue specimens. In addition, SILAC requires reverse labeling with an isotope set to ensure that differences in protein expression in different cell cultures are not caused by the different isotopes incorporated into the culture media. The present invention is an approach that permits quantitative measurements in cell culture, tissue biopsies, and all other conceivable biological, chemical, and environmental samples without the need to do any repetitious reverse labeling experiments that are necessary with SILAC.

The application of iTRAQ requires MS/MS or pulsed Q dissociation MS/MS/MS to fragment reporter tags, whereas the present invention is compatible on a broader range of instruments including instruments that perform MS only. In addition, the present invention requires no additional experimental steps that are required with using the iTRAQ labeling technology.

The compositions of the chemical reporter set included in the present invention include, but are not limited to, the following characteristics or properties. The inventive chemical reporter peaks overlap in such a way that they provide a continuous set of reporters during a fraction of, or the complete elution range of chemical or biological compounds fractionated by chromatography. The next important feature of the chemical reporter set is that these compounds are not present in the samples undergoing analysis. An embodiment of an inventive chemical reporter set is illustratively described in example 1 and shown in FIG. 3 and FIG. 4.

Chemicals present in an inventive chemical reporter set include, but are not limited to the following classes of chemicals including: alcohols, esters, amines, organic acids, organic bases, ethers, sulfones, acetylenes, adamantanes, anthracenes, pyrones, benzoquinones, anthraquinones, hydrocarbons, pyrrolidines, imides, indoles, quinolines, azulenes, carbazoles, hydroxylamines, nitriles, stilbenes, metallocenes, quaternary ammonium compounds, imidazolium compounds, pyridinium compounds, phosphonium compounds, halides, phenols, aldehydes and ketones. However any class of chemical compound may be used for the purposes described herein.

A biological reporter set may be comprised of the following non-limiting examples including nucleotides, oligonucleotides, sugars, lipids, fats, proteins, metabolites, and peptides that are useful for standardizing mass spectrometry detection efficiency. The following provides specifications relevant for the composition of a biological reporter set useful for making quantitative measurements with mass spectrometry. An artificial peptide of the present invention may have an engineered sequence based on the hydropathic nature of the amino acids present in the sequence, peptide sequence length, and sequence of amino acids within a peptide to create overlapping peptide reporter peaks that elute continuously from chromatographic columns for a fraction of, or the complete elution range of chemical or biological compounds. An example of a set of variable hydropathic index peptides is shown in FIG. 7 along with their elution times under specified conditions predicted by the Sequence Specific. Retention Calculator version 3.0, FIG. 10-FIG. 13 shows the continuous peak to peak elution pattern of these artificial peptides. As used herein "continuous" or "continuously" when used in reference to the elution of the reporters from a chromatographic column (such as but not limited to, a liquid chromatography column) refers to the elution of given number of reporters over a set unit of time during the elution profile such that an analyte to be quantified is likely to co-elute with a reporter. In one embodiment, the set unit of time is at least every 6 seconds, at least every 12 seconds, at least every 18 seconds, at least every 24 seconds or at least every 30 seconds over at least a portion of the elution profile. In a specific embodiment, the set unit of time is at least every 10 seconds or at least every 12 seconds over at least a portion of the elution profile. As used herein "at least a portion of the elation profile" means the entire elution profile or a portion thereof, for example at least during 1 minute of the elution profile, at least during 2 minutes of the elution profile or at least during 3 minutes of the elution profile. Various reporters, whether chemical or biological, can be designed as described herein to provide such a continuous elution profile. The sequences of the proteolytic fragments generated from the artificial protein set or any combination of proteins/peptides described in the present invention are either not present in the samples being analyzed and/or not predicted to exist or be created through proteolytic digestion with the endoproteinase used to digest sample proteins. An illustrative example of a list of artificial peptides that are incorporated into an artificial protein and its corresponding proteolytic fragments that are not present in sequenced genomes or expected to be generated by trypsin hydrolysis are shown in FIG. 7. In one embodiment, the artificial protein has the following general structure: $L_1\text{-}[K/R\text{—}(X)_n\text{—}K/R\text{-}L_2]_a$ wherein $L_1$ and $L_2$ are each linkers which can be the same or different and $L_2$ can vary for each repeating group, n is from 1 to 1000 and a is from 2 to 1000.

FIG. 8 provides one embodiment of an amino acid sequence of such an artificial protein that falls within this general formula. In another embodiment, the artificial protein has the following general structure: $L_1\text{-}[R\text{—}(X)_n\text{—}R\text{-}L_2]_a$, wherein $L_1$ and $L_2$ are each linker which can be the same or different and $L_2$ can vary for each repeating group, n is from 1 to 1000 a is from 2 to 1000 and at least one of the repeating groups $(X)_n$ comprises a sequence K-P and the artificial protein is subject to guanidination on the K residues. In one embodiment, all the repeating groups $(X)_n$ comprises a sequence K-P. It is noted that the sequence of the linker regions may be designed as discussed herein to vary the isoelectric point of the artificial protein or the molecular size of the artificial protein. The linkers in the artificial protein are cleavable to allow release of the individual reporter peptides (i.e., the linker is a cleavable linker). The linkers may be cleaved by chemical or biological means. In one embodiment, the linker sequences may contain a proteolytic digestion site that is a target for an endoproteinase selected from the group consisting of trypsin, chymotrypsin, Lys-C, Glu-C, Asp-N proteinase K, V-8 protease, Arg-C or Pro-C; in a specific embodiment the proteolytic digestion site that is a target for trypsin endoproteinase. In addition, in one embodiment, linkers may have an acidic character. These modifications will not impact the reporter peptides contained therein to be used as described herein. In the foregoing, it is understood that R represents the amino acid arginine, K represents the amino acid lysine and P represent the amino acid proline. These aspects are provided in Schemes 1-4 (FIGS. 22-25). The molecular ion m/z values of the unfragmented peptides generated from the artificial proteins optionally contain 2 mass to charge values to provide a mechanism to detect interference in the reporter peptides when using molecular ion MS1 spectra for quantification. The 2 highly basic amino acids lysine and arginine and the peptide N-terminus are each capable of accepting a proton, which generate doubly $[M+2H]^{+2}$ and triply $[M+3H]^{+3}$ charged molecular ions. The proline residue immediately C-terminal to the lysine residue prevents trypsin hydrolysis at the C-terminus of lysine, permitting the generation of the K(guanidinated)-P—$(X)_n$—R sequence in experiments with trypsin. As used here "interference" means another ion that is not a reporter peptide but contributes to the signal generated for a reporter peptide. The ratio between the doubly and triply charged molecular ions of the artificial peptide reporters provides a mechanism for determining if m/z signal interference is occurring from co-eluting compounds in samples. Interference can be detected when the ratio of the two charge states for a reporter peptide differs between a solution of the reporter peptides alone or in the presence of purified standard compounds, and the reporter peptides in an experimental sample. When interference is detected, the molecular ion charge state signal for the reporter peptide is used with the greatest decrease or smallest increase in the experimental sample relative to the solution of reporters alone or in the presence of purified standard compounds. The artificial peptide reporters also contain a fragment ion m/z value that is not predicted to be created from the fragmentation of natural peptides from samples undergoing analysis. This eliminates the possibility that the signal from a natural peptide in the sample would be mistakenly included as part of the signal from a reporter peptide. To obtain an unnatural fragment m/z, the artificial proteins will be subjected to guanidination. This will convert the lysine residue present in each peptide to homoarginine. The N-terminus of the artificial proteins will also be guanidinated, but the corresponding peptide will not be used in the method. The guanidination reaction may be performed using O-methylisourea with 1 heavy atom to create a mass increase of 43 Daltons. The 144 m/z a-1 fragment ion created by using a heavy atom in the O-methylisourea does not correspond to the m/z found in any a, b, or y singly charged fragment ion in any peptide composed of the common amino acids, or that might be produced by loss of $NH_3$ or $H_2O$ from the common amino acids. In addition, the 144 m/z fragment does not correspond to any internal fragment with a single side chain formed by the combination of a and y type cleavage immonium ions. Previous studies have shown that guanidination of lysine residues results in a chemically stable product with an increase in basicity and MS signal intensity in MALDI-TOF spectra (Brancia, F L, et al *Electrophoresis*, 2001; 22: 552-559). It is appreciated that other modifications or peptide sequences may be used to produce unique fragment peptide m/z values that are within the scope and spirit of the present invention.

Embodiments of the artificial peptides or artificial proteins can include variants having 0% to 100% sequence identity to naturally occurring amino acid sequences with the proviso that the artificial or naturally occurring peptide reporters are not present in the experimental sample undergoing analysis.

An inventive artificial peptide or set of artificial peptides is appreciated to be different from any peptide expected to be present in a sample for analysis. Illustratively, each inventive peptide shows less than 100 percent sequence identity to any region of any peptide or protein in an analytical sample undergoing analysis. It is appreciated that a single amino acid substitution to a naturally occurring amino acid or non-naturally occurring amino acid is sufficient to confer difference to an inventive peptide sequence.

Amino acids present in an inventive peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, alto-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylomithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the terms "inventive peptide" or "inventive protein" as used herein include peptides or proteins having between 2 and about 1000 amino acids or having a molecular weight in the range of about 100-350,000 Daltons.

Art inventive peptide is obtained by any of various methods known in the art illustratively including isolation from a cell or organism, chemical synthesis, expression of a nucleic acid and hydrolysis of proteins. Chemical methods of peptide synthesis are known in the art and include solid phase peptide synthesis and solution phase peptide synthesis. The term "naturally occurring" refers to a peptide endogenous to a cell, tissue or organism and includes allelic variations. A non-naturally occurring peptide is synthetic or produced apart from its naturally associated organism or is modified and is not found in an unmodified cell, tissue or organism.

In some embodiments, the artificial proteins are produced in truncated versions and with mass altering amino acids that are not used in the mass spectrometric analysis, but function to alter the molecular size of artificial proteins when separated by electrophoresis to permit the creation of various molecular weight versions of the artificial proteins that each have the identical set of reporters. Illustratively, an inventive artificial protein with a molecular weight of 200,000 may contain the complete reporter set in a single protein with or without the need of adding additional peptides in the protein for the purpose of altering the mass of the protein. The artificial proteins with a molecular weight of 20,000 may illustratively contain the complete reporter set in a cocktail of several artificial proteins with or without the use of mass altering amino acids that will be used for the singular purpose of making the artificial proteins a specific molecular weight. The artificial proteins with various molecular weights are then applicable for use in shotgun proteomics experiments where samples are separated by SDS-PAGE with the artificial proteins present at the various molecular weight regions within the gel that will be excised with each excised region containing a set of reporters. The excised gel regions are then subjected to in-gel digestion protocols resulting in peptides that are fractionated by chromatography followed by mass spectrometric analysis.

It is known that the migration of a polypeptide can vary, sometimes significantly, with different conditions of SDS/PAGE (Capaldi et al, *Biochem. Biophys. Res. Comm.*, 1977; 76: 425). It will therefore be appreciated that under differing electrophoresis conditions, the apparent molecular weights of purified or partially purified expression products may vary.

The artificial proteins may contain amino acids for the purposes of adjusting the isoelectric point of the protein. For instance, the artificial peptide reporters may have high basic character for optimal observability in positive ion mode when placed in acidic ion pairing agents such as formic acid. The high basic character of the artificial peptide reporters correspondingly cause the artificial protein to have a high isoelectric point which may be unfavorable for protein expression. Thus "linker sequences" with high acidic character may be used as shown in example 2 to neutralize the protein. The linker sequences are not intended for downstream mass spectrometry applications. Additionally, the linker sequences can be used to control the isoelectric point of the artificial proteins for use with isoelectric focusing, where the artificial proteins are separated into the distinct isoelectric point regions.

In some embodiments, the complete artificial protein set is proteolytically fragmented and spiked into samples that have been proteolytically fragmented immediately prior to reverse phase liquid chromatographic separation and subsequent analysis by mass spectrometry as shown in example 2. In these instances, the artificial proteins provide standardization of the mass spectrometric detection efficiency in different samples, although it does not allow normalization of sample loss during sample preparation. This application of the present invention is instantly relevant for use in all experiments wherein biomolecules as well as organic and inorganic molecules are fractionated by liquid chromatography and analyzed by mass spectrometry. Several specific examples include but are not limited to proteins separated by native 1-D and 2-D protein gels and subsequent proteolytic fragmentation and in-solution proteolytic fragmentation of samples. In all instances, by spiking into samples an equivalent amount of the proteolytically fragmented artificial peptide set the mass spectrometric detection efficiency can be standardized in different samples.

An inventive artificial protein or artificial peptide is illustratively recombinant. An inventive artificial protein or artificial peptide may be expressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to an artificial protein or artificial peptide or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

It is appreciated that an inventive artificial protein or artificial peptide is optionally not tagged. In this embodiment and other embodiments purification is optionally achieved by methods known in the art illustratively including ion-exchange chromatography, affinity chromatography using specific antibodies, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

An inventive artificial protein or artificial peptide is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis, Illustrative methods of chemical protein synthesis are reviewed by Miranda, L P, *Peptide Science*, 2000, 55:217-26 and Kochendoerfer G G, *Curr Opin Drug Discov Devel*. 2001; 4(2):205-14, the contents of which are incorporated herein by reference.

Protein expression is illustratively accomplished by transcription of a nucleic acid sequence encoding an artificial protein or artificial peptide followed by translation of the RNA transcript produced. Protein expression is optionally performed in a cell based system such as in *E. coli*, Hela cells, or Chinese hamster ovary cells. It is appreciated that cell-free expression systems are similarly operable.

It is recognized that numerous variants, analogues, or homologues are within the scope of the present invention including amino acid substitutions, alterations, modifications, or other amino acid changes. Several post-translational modifications are similarly envisioned as within the scope of the present invention illustratively including phosphorylation, glycosylation, addition of pendent groups such as biotynlation, fluorophores, lumiphores, radioactive groups, antigens, or other molecules with the proviso that the substitutions create artificial proteins, artificial peptide reporters, or other artificial or natural biomolecules expected to be absent in samples being evaluated by mass spectrometry.

Further aspects of the present disclosure concern the purification, and in particular embodiments, the substantial purification, of an artificial protein or artificial peptide. The term "purified" or "isolated" protein or peptide as used herein, is intended to refer to a composition, isolatable from other components, wherein the artificial protein or artificial peptide is purified to any degree.

Generally, "purified" or "isolated" will refer to a protein or peptide composition that has been subjected to fractionation to remove various other components, and whose composition substantially retains its mass spectrometry detection efficiency function. Where the term "substantially" purified is used, this designation will refer to a composition in which the protein or peptide forms the major component of the composition, such as constituting about 50% or more of the proteins in the composition.

Various techniques suitable for use in protein purification will be well known to those of skill in the art. These include, for example, precipitation with ammonium sulfate, polyethylene glycol, antibodies, or by heat denaturation followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme.

The nucleotide sequences of the invention, including fragments thereof and modifications thereto, may be constructed recombinantly using conventional genetic engineering or chemical synthesis techniques or PCR, and the like. They may be amplified for use by conventional uses of polymerase chain reaction or cloning techniques such as those described in conventional texts.

An inventive nucleic acid sequence encoding an inventive peptide is optionally isolated from the cellular materials with which it may be naturally associated. Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression.

Numerous agents are amenable to facilitate cell transfection illustratively including synthetic or natural transfection agents such as electroporation, calcium phosphate, LIPO-FECTIN, baculovirus, naked plasmid or other DNA, or other systems known in the art.

The present invention also includes a nucleic acid sequence encoding an inventive artificial protein or artificial peptide. The design of nucleic acid sequences to encode a particular protein or peptide sequence are known in the art from the standard understanding of the standard genetic code. Thus, any given desired artificial protein or artificial peptide sequence can be readily encoded by a nucleic acid sequence by one of ordinary skill in the art.

The present invention also provides a vector with a nucleic acid sequence encoding an inventive artificial protein or artificial peptide sequence therein. Illustrative vectors include a plasmid, cosmid, viruses with RNA or DNA genetic material or other vector systems known in the art. A vector is preferably a plasmid. A vector illustratively contains a selection marker such as an antibiotic resistance gene and a promoter for driving expression of a cloned sequence.

Also provided is a host cell transformed with an appropriate vector or with the inventive nucleic acid sequence encoding an inventive artificial protein or artificial peptide sequence therein. A host cell illustratively includes $E.\ coli$ or Sf9 cell. Optionally cell transformation is achieved by electroporation.

A method is also provided for recombinantly expressing an inventive nucleic acid or protein sequence wherein a cell is transformed with an inventive nucleic acid sequence and cultured under suitable conditions that permit expression of an inventive nucleic acid sequence or protein either within the cell or secreted from the cell. Cell culture conditions are particular to cell type and expression vector. Culture conditions for particular vectors and cell types are within the level of skill in the art to design and implement without undue experimentation.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning; A Laboratory Manual $3^{rd}$ ed. (Cold Spring Harbor, N.Y. 2001), the contents of which are incorporated herein by reference).

The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino acid sequences. A recombinant polynucleotide of the present invention may be produced and used with or without introns.

To express a recombinant encoded polypeptide in accordance with the present invention one would prepare an expression vector that comprises a polynucleotide under the control of one or more promoters. To bring a coding sequence "under the control of" a promoter, one positions the 5' end of the transcriptional initiation site generally between about 1 and 50 nucleotides "downstream" of (i.e., 3' of) the chosen promoter. The "upstream" promoter stimulates transcription of the inserted DNA into RNA, which is subsequently translated into protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as $E.\ coli$ and $B.\ subtilis$ transformed with recombinant phage DNA, plasmid DNA or cosmid DNA expression vectors.

Certain examples of prokaryotic hosts are $E.\ coli$ strain RR1, $E.\ coli$ LE392, $E.\ coli$ B, $E.\ coli$ .chi. 1776 (ATCC No. 31537) as well as $E.\ coli$ W3110 (F-, lambda-, prototrophic, ATCC No. 273325); bacilli such as $Bacillus\ subtilis$; and other enterobacteriaceae such as $Salmonella\ typhimurium$, $Serratia\ marcescens$, and various $Pseudomonas$ species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, $E.\ coli$ is often transformed with plasmids derived from pBR322, a plasmid derived from an $E.\ coli$ species. These plasmids contain genes for resistance to one or more antibiotics, such as ampicillin and tetracycline, which provide an easy means for identifying transformed cells. The plasmids, or other microbial expression vectors must also contain, or be modified to contain, promoters that can be used by the microbial organism for expression of proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as $E.\ coli$ LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Non-limiting examples of promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in $Saccharomyces$, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, MK, COS-7, 293, HepG2, NIH3T3, RIN and MDCK. In addition, a host cell may be chosen that modulates the expression of the inserted sequences, or modifies and processes the gene product in the specific fashion desired.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter).

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus or pre-existing plasmids as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position appropriate for transcription termination [the poly A IS the transcription termination signal].

For long-term, high-yield production of recombinant proteins, stable expression is preferred. For example, cell lines that stably express constructs encoding proteins may be engineered. Rather than using expression vectors that contain viral origins of replication, host cells can be transformed with vectors containing appropriate expression control elements (e.g., promoter, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited to, the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated nucleic acids of the disclosure may be "overexpressed", relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot.

Methods involving conventional biological techniques are described herein. Such techniques are generally known in the art and are described in detail in methodology treatises such as Molecular Cloning: Laboratory Manual, 2nd ed. vol, 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Some Applications of the Present Invention.

In some embodiments the present invention provides tools and methods for quantifying the relative levels of many biomolecules in different samples. Proteins can be identified based upon the proteolytic fragments obtained by LC/MS to have m/z's that are diagnostic for a particular protein, and referred to in the field as a peptide mass fingerprint. MS1 spectra can be plotted as a chromatographic map in which the signal intensity for a given m/z value is plotted versus the time of its detection; i.e., the time it elutes from an LC column. Each sample peptide m/z peak is then checked to determine which partially or completely co-fractionating artificial peptide reporter(s) can be used for normalizing mass spectrometry detection efficiency, thus enabling quantitative comparisons between samples that differ in their matrix effects.

Pure biomolecule standards of known concentration used for absolute or relative quantification of targeted biomolecules in conjunction with the use of the present invention may be chemically synthesized or prepared using molecular biology recombinant methods.

Pure chemical standards of known concentration may be used with the present invention for absolute or relative quantification of targeted chemicals.

Compatible samples in accordance with the present invention include but are not limited to biological cells, cell supernatants, cell extracts, cell lysates, viruses, biological fluids and tissues, organs, organisms, serum, blood samples, as well as organic and inorganic molecules.

Biomolecules including proteins are optionally quantified from samples from a healthy subject and optionally compared to proteins quantified in samples from one or more subjects with disease or abnormality. The comparison of protein levels caused by protein expression and degradation mechanisms may reveal proteins important for physiological homeostasis or pathogenesis, and thereby identify proteins that aid in the evaluation of susceptibility or diagnosis of disease. Also, the present invention may also aid in the identification of therapeutic targets of disease.

The present invention is particularly useful in the field of biomarkers for assessing and diagnosing disease. The potential for increased sensitivity of the present invention relative to iTRAQ and SILAC due to the absence of sample mixing may permit the detection of biomarker proteins at earlier stages of disease processes.

Some embodiments of the present invention are applicable for drug and toxicology level measurements. For instance, the levels of a chemical compound in a biological sample can be determined by preparing a standard in which a known amount of the pure chemical is spiked with the biological or chemical reporters of the present invention. The relative MS peak areas obtained for this standard are then compared to those obtained when the biological sample is spiked with an identical amount of the chemical or biological reporters to normalize for mass spectrometric detection efficiency of the chemical compound in different samples.

In the pharmaceutical industry the present invention is particularly useful in drug development and drug discovery. For example, a pharmaceutical company's lead hits for treatment of a disease are often used as the starting point for the production of thousands of homologues, with the goal of obtaining a compound with more favorable characteristics, such as greater efficacy, increased biological half life and reduced toxicity. The present invention is useful with respect to half life measurements of the homologues in the blood or tissue of animals used in the studies. Although pharmaceutical companies may have an isotopically labeled standard of known concentration for their lead compound, it is not practical or cost effective to have isotopic standards for the thousands of homologues. The lack of appropriate standards for non-lead compounds may result in inaccurate quantification of the homologues in blood, urine, or tissues. The present invention provides a method to accurately quantify the levels of thousands of small molecule drug candidates without having to produce isotope standards for each compound or having to identify an appropriate co-fractionating standard by time consuming empirical testing.

Kits

The present invention includes kits for performing the methods, and/or kits that include several applications of the present invention.

Kits in accordance with the present invention optionally include the artificial protein reporter set at various molecular weights in Laemlli sample buffer to allow the addition of experimental samples prior to SDS-PAGE fractionation in differing concentrations of Laemlli buffer such as 2×, 3×, 4×, 5×, to enable consumers to select a particular concentration suitable for their experiments. Kits optionally include a molecular weight ladder indicating the exact position of artificial proteins following electrophoretic separation of the various molecular weight forms of the artificial proteins. Molecular weight ladders are sold by various vendors, illustratively, including the Benchmark™ protein ladder available from Invitrogen Corp., Carlsbad, C.A.

The inventive artificial proteins are optionally added directly to tissue or cell culture homogenate in a single molecular weight form compatible for experiments without size fractionation by SDS-PAGE. Alternatively, the artificial proteins can be added directly to tissue or cell culture homogenate in the various molecular weight forms for use in experiments with size fractionation by SDS-PAGE.

Additionally, the artificial protein is optionally proteolytically fragmented and sold in kits for use in experiments without electrophoretic separation or for use in measuring chemical molecules. The fragmented artificial protein is optionally spiked into samples prior to chromatographic fractionation followed by mass spectrometric analysis.

Various aspects of the present invention are illustrated by the following non limiting examples. The examples are for illustrative purposes and are not a limitation on any practice of the present invention. It will be understood that variations and modifications can be made without departing from the spirit and scope of the invention.

Example 1

An example of using a chemical reporter set to measure the absolute level of ranitidine in human plasma. An inventive set of chemical reporters of mass spectrometry detection efficiency were created based on their predicted ability to elute in a continuous peak to peak manner during a portion of an LC separation. The HPLC retention index (R.I.) of salbutamol (R.I. 225), 7-methylxanthine (R.I. 225), 4-aminoantipyrine (R.I. 226), famotidine (R.I. 228), DL-4-hydroxy-3-methoxymandelic acid (R.I. 230), and trans-2-phenylcyclopropylamine hydrochloride (R.I. 232) were previously described in Hill, D W, et al *J Anal Tox,* 1994:18:233-242. These chemical reporters were dissolved in 5% formic acid and mixed in said concentrations: salbutamol (2 nanograms/uL), 7-methylxanthine (12 nanograms/uL), 4-aminoantipyrine (10 nanograms/uL), famotidine (200 nanograms/uL), DL-4-hydroxy-3-methoxymandelic acid (18 nanograms/uL), trans-2-phenylcyclopropylamine hydrochloride (10 nanograms/uL). A 5 nanogram/uL solution of ranitidine was prepared by dissolving 5 milligrams of ranitidine in 1 mL of 5% formic acid followed by placing 1 uL of the 5 micrograms/uL in 999 uL of 5% formic acid. The 5 nanograms/uL solution of ranitidine was mixed with an equal volume of the said concentration of said chemical reporter set which reduced the concentration of the chemical reporter set and the ranitidine by half. LC/MS analysis in the multiple reaction monitoring mode was performed using an MDS Sciex/Applied Biosystems API 3200 mass spectrometer with a positive electrospray voltage of 5500 volts in the positive ion mode and a negative electrospray voltage of −4500 volts in the negative ion mode. A 40 millisecond dwell time was used for each transition corresponding to the chemical reporter set and ranitidine with a total cycle time of 1.705 seconds. The mass spectrometer was connected online to a Waters Acquity UPLC system with a Phenomenex $C_5$ reverse phase 2×250 millimeter column with a 0.2 milliliter/minute flow rate. The mobile phase A used was 0.1% formic acid and mobile phase B was 0.1% formic acid/methanol. The following 6 minute gradient and 4 minute column equilibration used were as follows: 0 minutes 20% B, 5 minutes=50% B, 5.1-6.0 minutes 100% B, 6.1-10 minutes=20% B. An injection volume of 10 uL was used in each analysis shown. FIG. 3. displays the chemical reporter set with 2.5 nanograms/microliter of ranitidine mixed with an equal volume of 0.1% formic acid. An identical concentration of the chemical reporter set and the ranitidine at 2.5 nanograms/uL were then mixed with an equal volume of human serum and the extracted ion chromatograms of the standard and ranitidine are shown in FIG. 4. The results showing the area under the curves and retention times of the chemical reporter set to normalize for mass spectrometry detection efficiency in human serum are shown in table 1.

TABLE 1

Results of experiment 1.

| | Chemical Reporter Set and ranitidine in 0.1% formic acid | | Chemical Reporter Set and ranitidine in human serum | |
|---|---|---|---|---|
| | AUC | Elution Time (minutes) | AUC | Elution Time (minutes) |
| Chemical Reporter Set | | | | |
| 4-aminoantipyrine | 4.18E+05 | 4.47 | 3.67E+05 | 4.49 |
| trans-2-phenylcyclopropylamine | 3.36E+05 | 5.14 | 3.27E+05 | 5.17 |
| salbutamol | 2.80E+05 | 4.05 | 1.24E+05 | 4.07 |
| 7-methylxanthine | 5.15E+05 | 4.5 | 3.94E+05 | 4.53 |
| famotidine | 1.77E+05 | 4.12 | 8.11E+04 | 4.18 |
| DL-4-hydroxy-3-methoxymandelic acid | 9.62E+04 | 4.55 | 9.17E+04 | 4.56 |
| Chemical Measured | | | | |
| ranitidine | 4.12E+05 | 4.13 | 1.77E+05 | 4.16 |

AUC = area under the curve in chromatogram.

Figure 5:
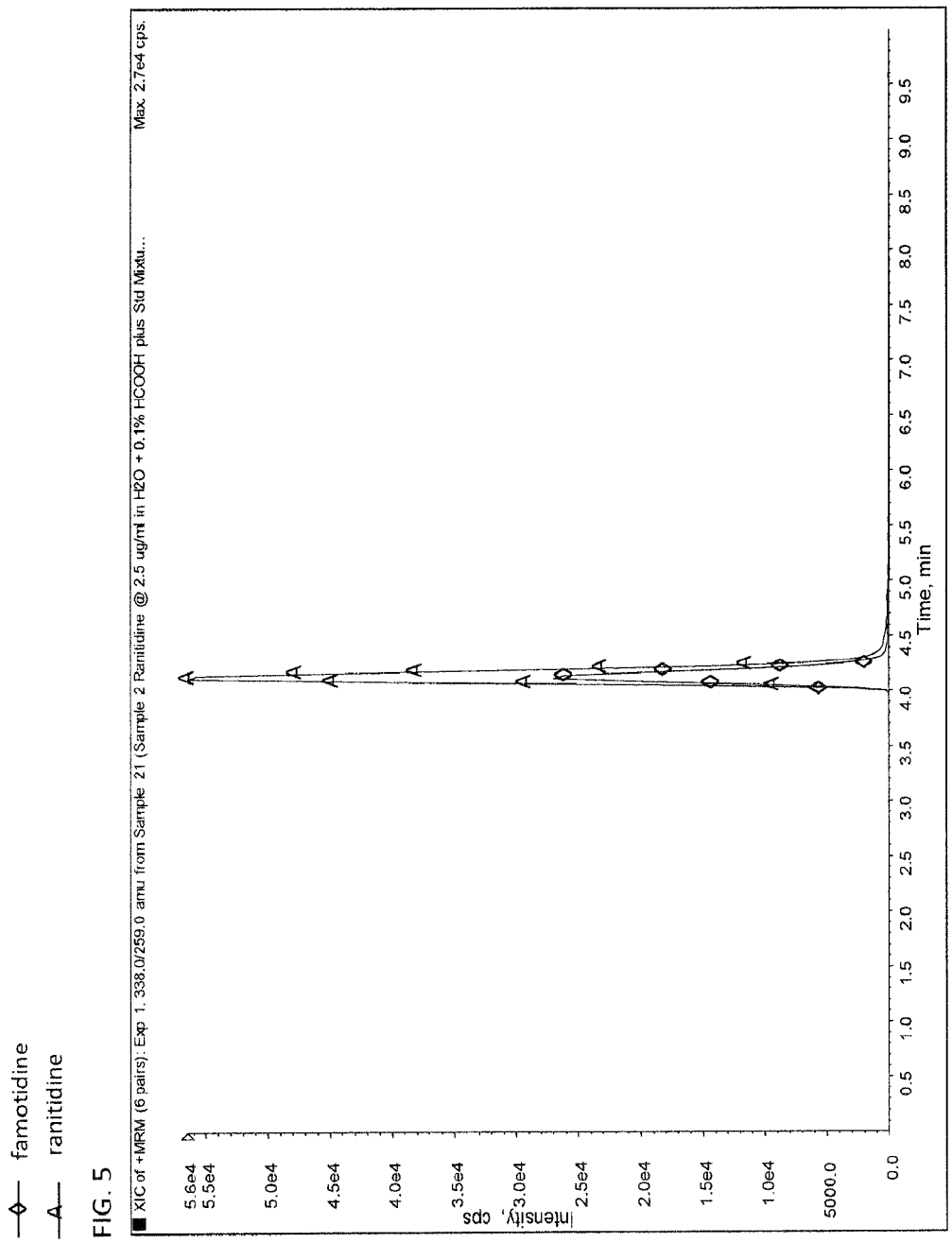
FIG. 5 shows the extracted ion chromatograms of ranitidine and the co-fractionating chemical famotidine from the chemical reporter set of FIG. 3 without the other chemical reporters that do not co-fractionate with ranitidine.
Figure 6:
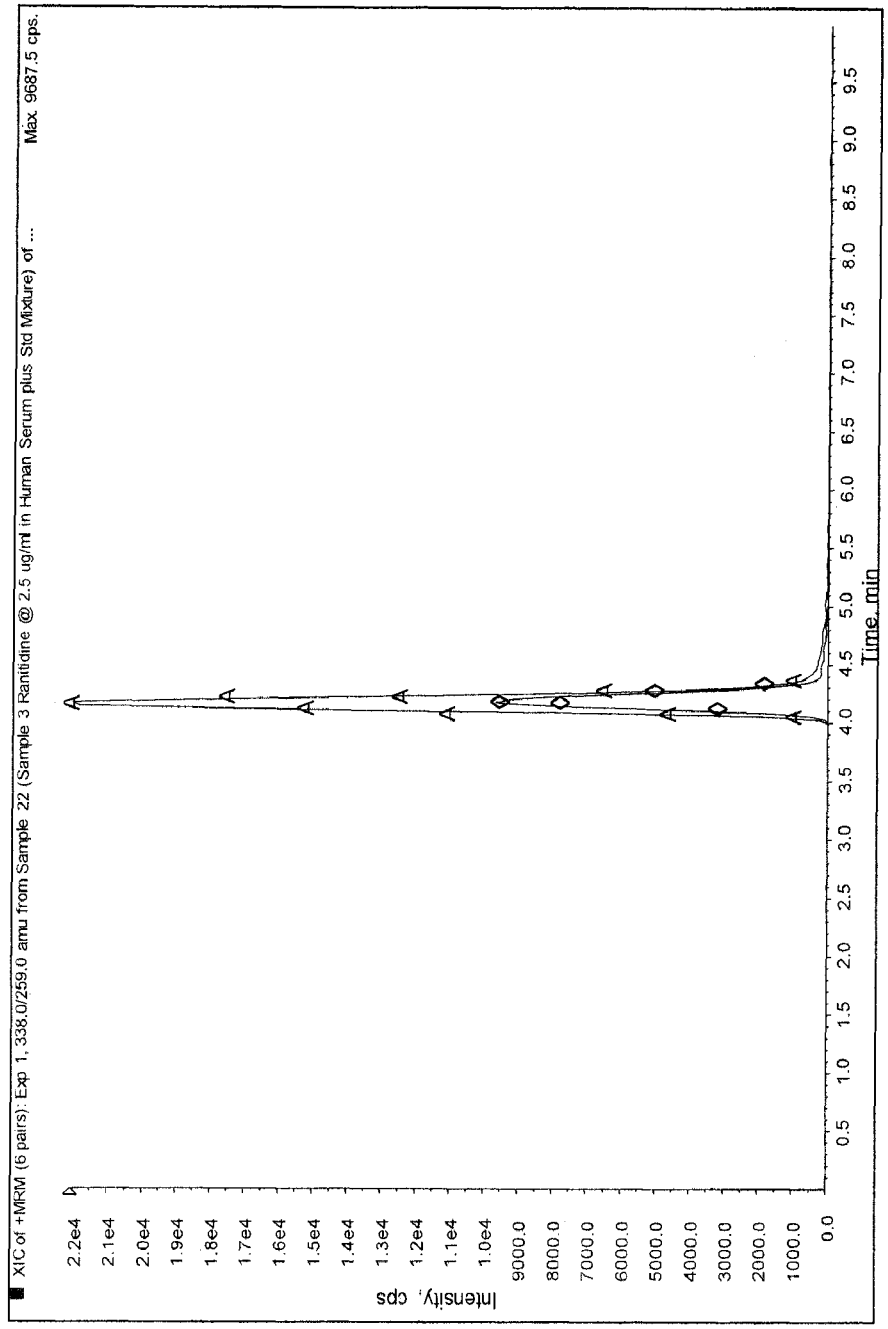
FIG. 6 shows the extracted ion chromatograms of ranitidine and the co-fractionating chemical famotidine from the chemical reporter set of FIG. 3 without the other chemical reporters that do not co-fractionate with ranitidine.

Next it was determined that famotidine in the chemical reporter set co-fractionated from the LC column with ranitidine. The amount of ranitidine in human serum can be calculated by comparing the area under the curve ratio of ranitidine/famotidine in the chemical reporter set with rantidine in 0.1% formic acid (4.12e5/1.77e5=2.327) to the ratio of ranitidine/famotidine in the human serum (1.77e518.11e4=2.182). The ratio of rantidine/famotdine in human serum divided by the ratio of rantidine/famotidine in 0.1% formic acid is 2.182/2.327=0.937. By multiplying 0.937×1.25 nanogram/uL ranitidine in 0.1% formic acid yields the value determined using the co-fractionating reporter famotidine of 1.171 nanogram/uL. This value is within 6.3% of the correct theoretical value, even with a significant reduction in signal strength of 57% caused by the complexity of the human serum. FIG. 5, shows the extracted ion chromatograms of ranitidine and the co-fractionating chemical famotidine from the chemical reporter set in 0.1% formic acid without the other chemical reporters that do not co-fractionate with ranitidine. FIG. 6. shows the extracted ion chromatograms of ranitidine and the co-fractionating chemical famotidine from the chemical reporter set in human serum at an identical concentration of ranitidine and the chemical reporter set without the other chemical reporters that do not co-fractionate with rantitidine.

Example 2

Design of artificial sequences: An in silico set of 20 artificial reporter peptides were created that were predicted by the Sequence Specific Retention Calculator Version 3.0 to elute in a peak to peak fashion during a fraction of the entire liquid chromatography separation with a 2% acetonitrile/minute linear gradient. These peptide sequences are shown in FIG. 7, and were checked to ensure that they do not exist in sequenced genomes by using the Prowl software program which searches sequenced genomes from the NCBI database (last updated on May 16, 2010) to ensure that the inventive peptides would not be generated by trypsin hydrolysis of proteins from the organisms of sequenced genomes. The peptides shown in FIG. 7. were assembled into an artificial protein and created by expression of the cDNA sequence shown in FIG. 8. This cDNA sequence was synthesized and subcloned into the NdeI and XhoI sites of the pET23b+ expression vector. A nucleotide sequence for protein expression of a 6×His tag was incorporated into the carboxyl terminus of the expressed protein. The corresponding sequence of the expressed protein from the cDNA sequence of FIG. 8. is shown in FIG. 9.

E. coli BL21 (λDE3) cells were transformed with the expression vector containing the cDNA sequence of FIG. 8. Cells were grown to an $A_{600}$ of 0.4 in 50 micrograms/uL of chloramphenicol and ampicillin in LB medium and protein expression was initiated by the addition of 1 mM IPTG for 4 hours at 37° Celsius. The cells were harvested by centrifugation at 4,000 r.p.m, for 15 minutes at 22° Celsius. The supernatant was discarded and the pellet was subjected to 3 freeze thaw cycles by placing in a −80° Celsius freezer. The thawed bacterial pellet was then Dounce homogenized in 10 mM Tris-HCl, pH 8.0, 5 mM EDTA. 100 mM NaCl, 1 mM PMSF and incubated on ice far 15 minutes followed by centrifugation at 30,000×g for 30 minutes at 4° C. The supernatant was discarded and the pellet homogenized in 10 mM Tris-HCl, pH 8.0, 5 mM EDTA, 100 mM NaCl, 1 mM PMSF, 1.5M KCl, 1% Triton X-100 followed by centrifugation at 30,000×g for 20 minutes at 4'C. The supernatant was discarded and the pellet Dounce homogenized a second time in 10 mM Tris-HCl, pH 8.0, 5 mM EDTA, 100 mM NaCl, 1 mM PMSF, 1.5M KCl, 1% Triton X-100 followed by centrifugation at 30,000×g for 20 minutes at 4° C. The supernatant was discarded and the pellet was washed 3 times with MilliQ water to remove excess salts followed by dissolving the pellet in 50 mM sodium phosphate, 300 mM sodium chloride, 6M guanidine hydrochloride, 10 mM imidazole, pH 7.4. Purification using a cobalt HisPur-spin column (Thermo Scientific, Rockford, Ill.) was performed according to the manufacturer's instructions. The HisPur-spin column elution fractions were dialyzed into 10 mM Tris-HCl. 6M urea, pH 8.0 for 12 hours at 4° C. The concentrations of the dialyzed fractions were determined using the Bicinchoninic acid assay. 1 ug of the purified protein from each fraction or the maximum amount of volume was loaded in a 4-20% gradient SDS-PAGE gel and separated according to molecular weight. The appearance of a highly pure protein at the expected 30 kD molecular size was visualized in the first elution fraction of purified protein after Coomassie R-250 staining and destaining with methanol/acetic acid. This protein was used in subsequent experiments.

A gel slice representing the 30 kD molecular weight range was excised from the gel. The gel piece was then minced into 1-$mm^3$ pieces and washed three times with 50% acetonitrile, 25 mM ammonium bicarbonate, pH 8.0, thr 15 minutes followed by a final wash overnight for 15 hours. The samples were then dehydrated with 100% acetonitrile for 5 minutes and dried under vacuum by rotary evaporation for 25 minutes. A 20 uL solution of 1 nanogram/uL sequencing grade trypsin in 100 mM ammonium bicarbonate, pH 8.0 was added to the dried gel pieces along with an additional 30 uL of 100 mM ammonium bicarbonate, pH 8.0 to completely cover the gel slices in liquid. Trypsin digestion was performed for 15 hours at 37° C. The resulting artificial peptides from the gel pieces were extracted from the gel by removal of the liquid phase to a second siliconized Eppendorf tube and replaced with 50 uL of 50% acetonitrile/5% formic acid followed by incubation at ambient temperature for 60 minutes. The resulting supernatant was removed, added to the sample collected previously. The supernatants were then pooled and dried under vacuum by rotary evaporation for 45 minutes. The lyophilized artificial peptides were then resuspended in 30 uL of 0.1% formic acid to create an artificial peptide standard concentration of 33.3 nanograms/uL. Then 9 uL of the 33.3 nanograms/uL artificial peptide digest was diluted in 91 uL of 0.1% formic acid to create a final concentration of 3 nanograms/uL or 100 femtomoles/uL of artificial peptides that were used in subsequent experiments.

Figure 10:
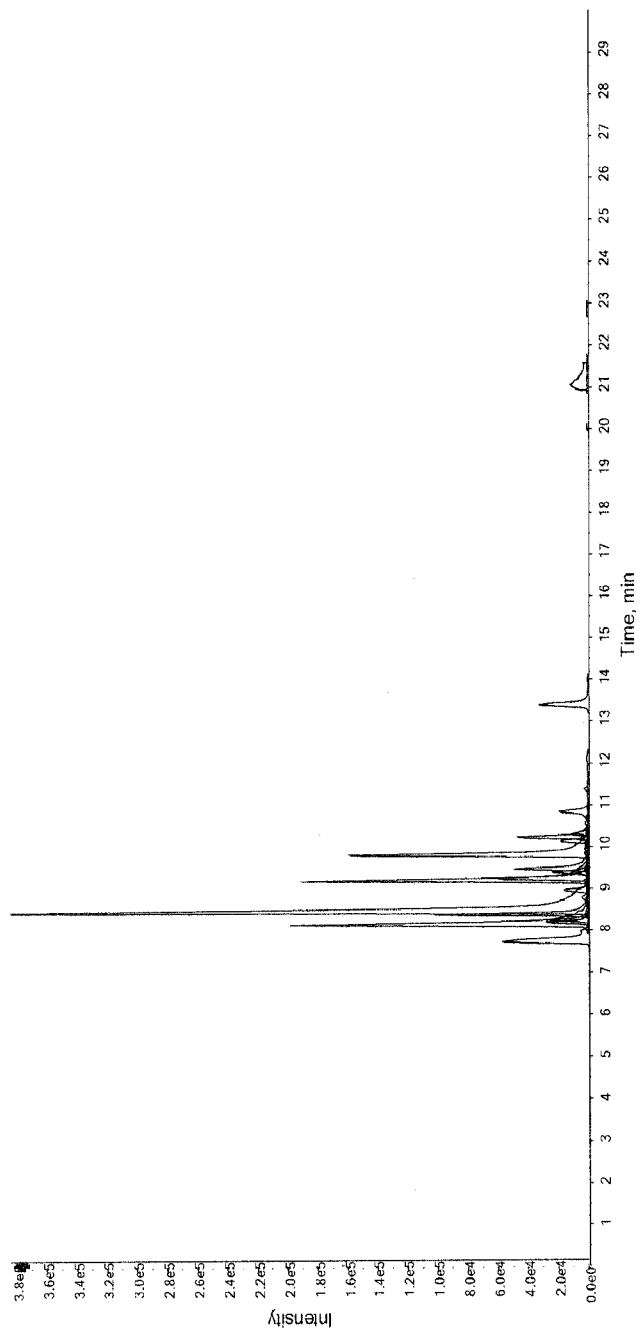
FIG. 10 shows an MS1 chromatogram of one embodiment of doubly charged reporter peptides of the present disclosure
Figure 11:
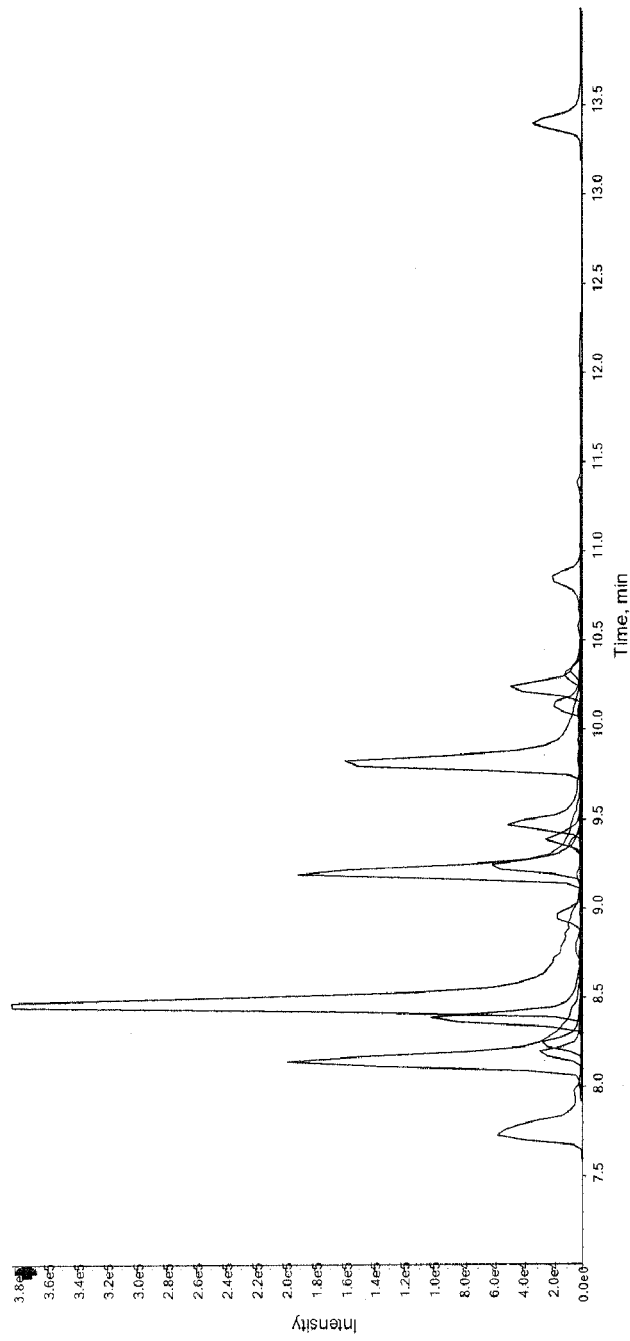
FIG. 11 shows the chromatogram of FIG. 10 in more detail.
Figure 12:
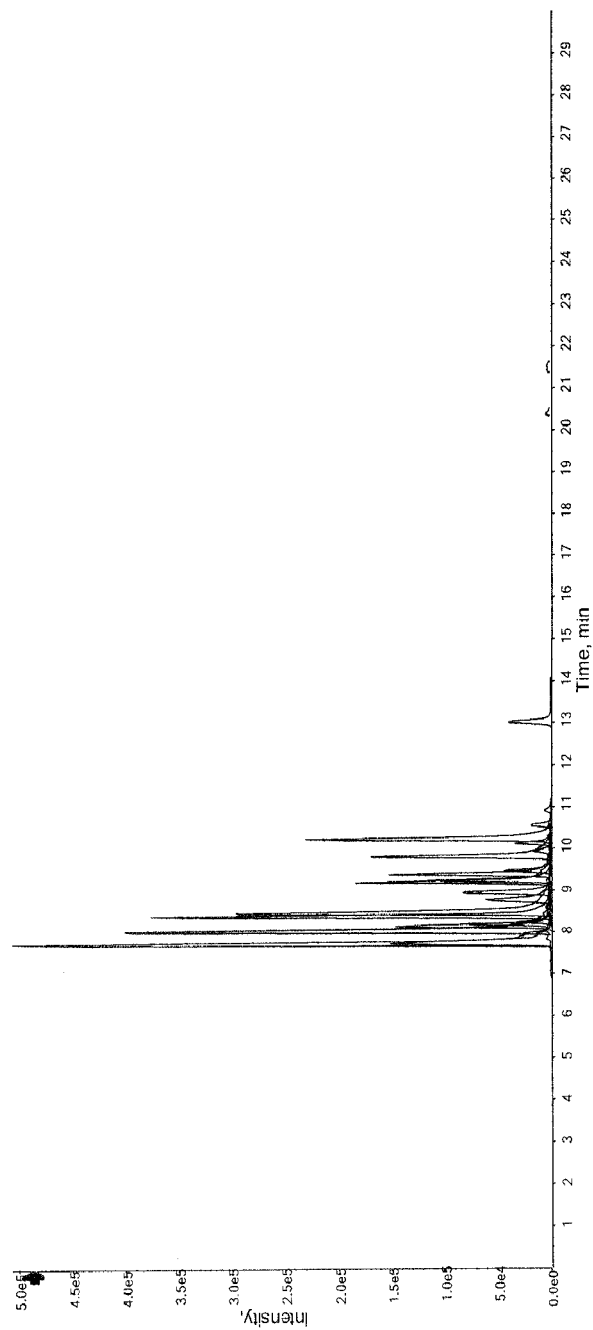
FIG. 12 shows an MS1 chromatogram of one embodiment of triply charged reporter peptides of the present disclosure
Figure 13:
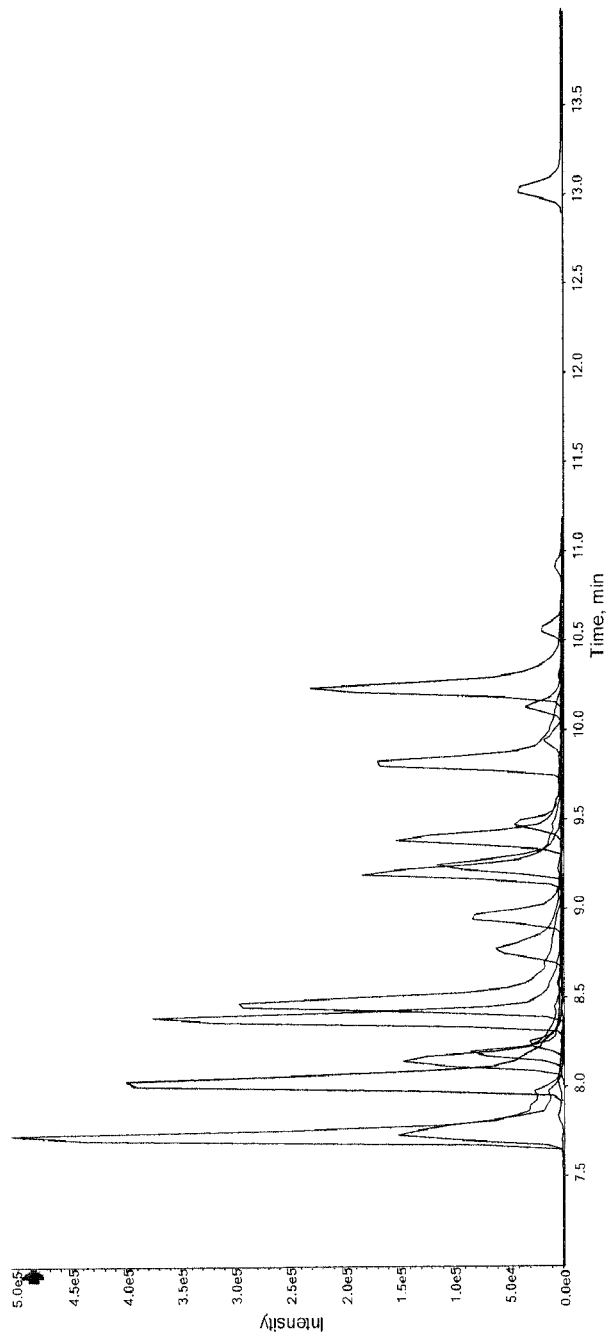
FIG. 13 shows the chromatogram of FIG. 12 in more detail.
Figure 14:
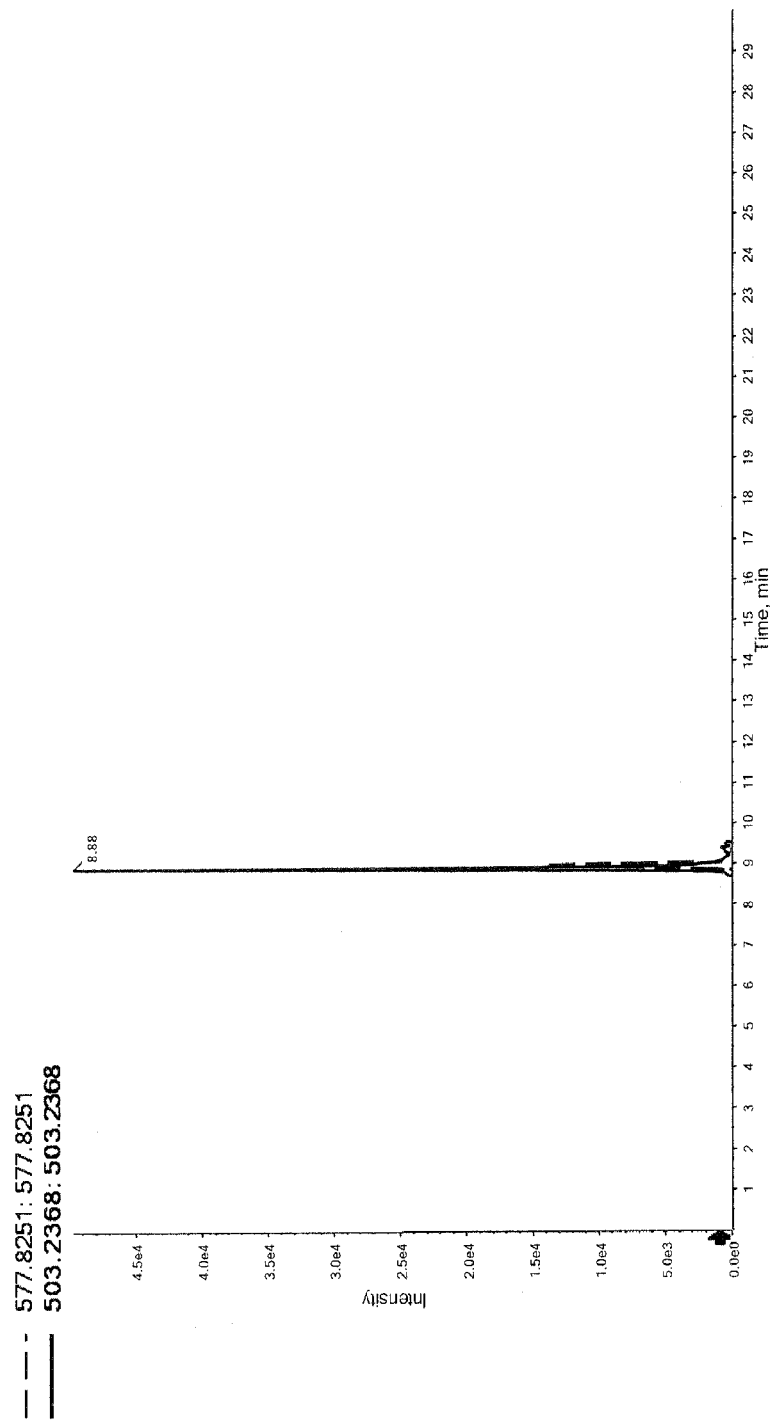
FIG. 14 shows a chromatogram of a beta-galactosidase peptide (YSQQQLMETSHR) co-fractionating with a reporter peptide (KPAAAAAAAAWR) in solution A (Solution A-12.5 femtomoles/uL of $E.\ coli$ beta galactosidase, 2.5 femtomoles/uL of bovine serum albumin and 100 femtomoles/uL of the artificial protein trypsin digest).
Figure 15:
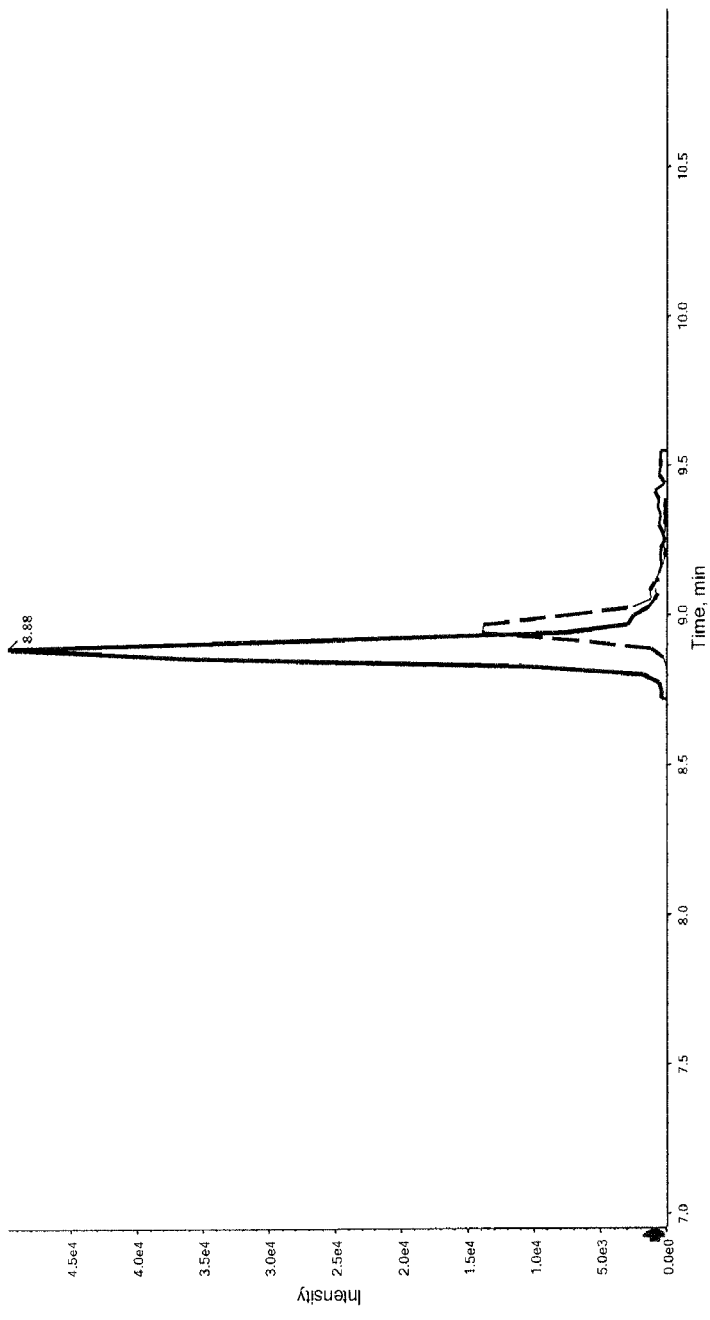
FIG. 15 shows the chromatogram of FIG. 14 in more detail.
Figure 16:
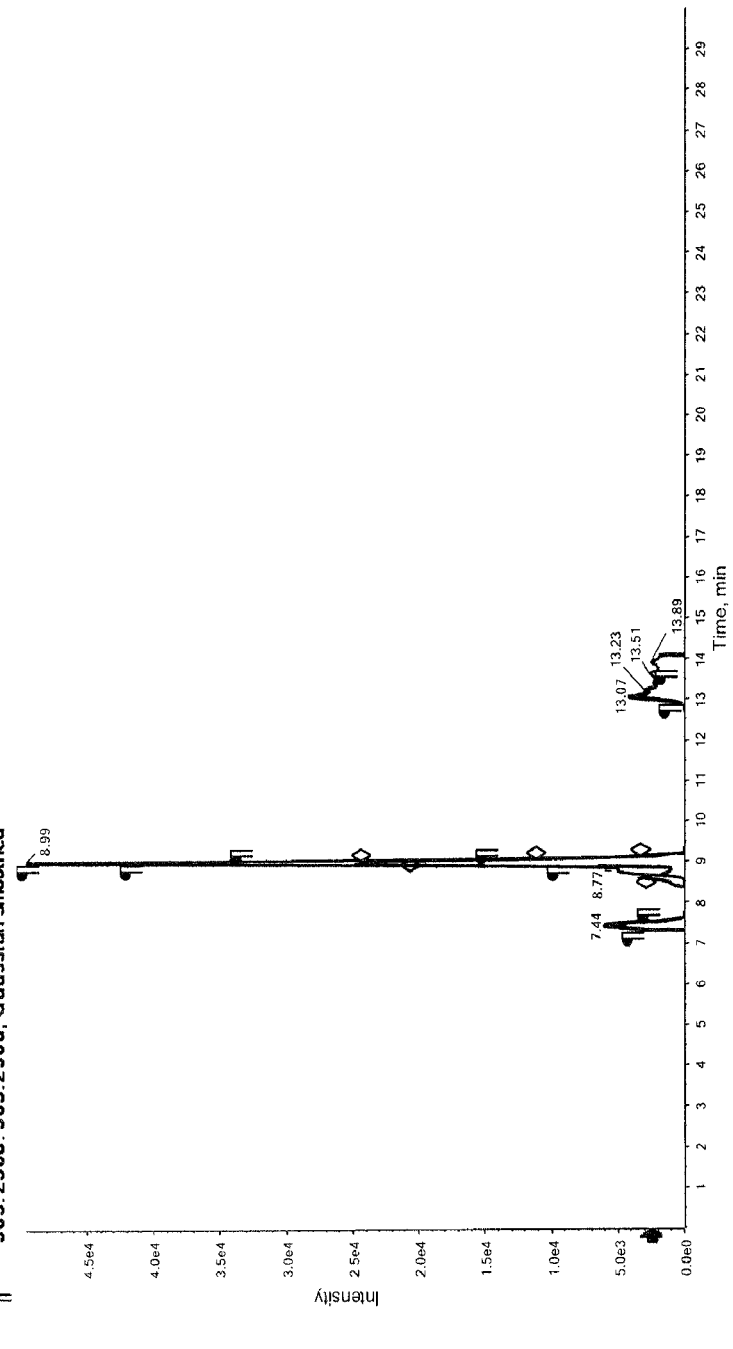
FIG. 16 shows a chromatogram of a beta-galactosidase peptide (YSQQQLMETSHR) co-fractionating with a reporter peptide (KPAAAAAAAAWR) in solution B (Solution B-125 nanograms/uL of soluble mouse digest, 12.5 femtomoles/uL of $E.\ coli$ beta galactosidase, 2.5 femtomoles/uL of bovine serum albumin and 100 femtomoles/uL of the artificial protein trypsin digest).
Figure 17:
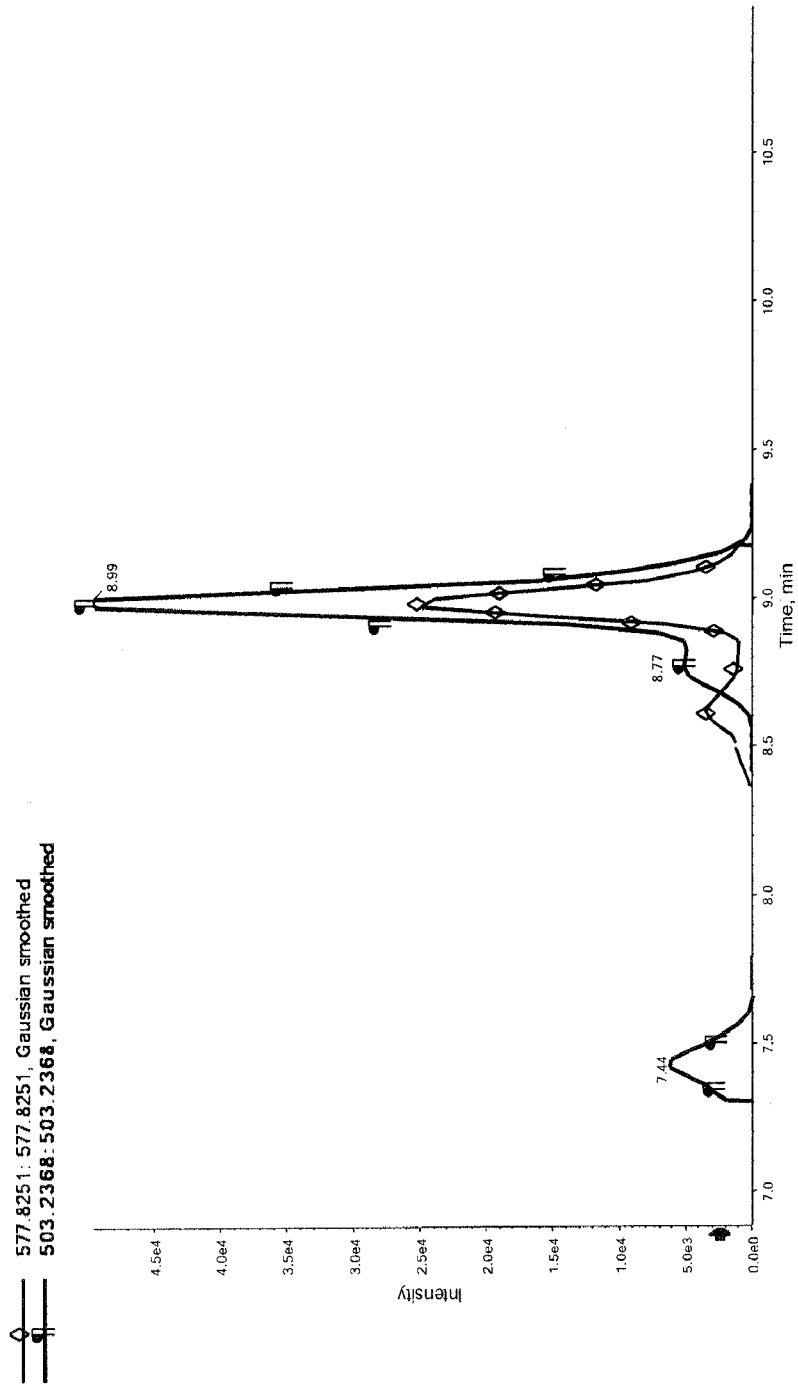
FIG. 17 shows the chromatogram of FIG. 16 in more detail.

Absolute quantification of E. coli beta-galactosidase and bovine serum albumin in 250 nanograms/uL of soluble mouse brain trypsin digest. Soluble mouse brain was prepared by Dour=homogenization in 100 mM Tris-HCL/6M urea, pH 8.0 buffer and centrifuged at 4° C. for 15 minutes at 13,000×g and the supernatant was collected as the soluble fraction. A Bicinchoninic acid assay was used to determine the concentration of the soluble mouse protein and the soluble mouse protein solution was diluted with 100 mM Tris-HCl/6 M urea, pH. 8.0 buffer to 5 micrograms/uL. A 100 uL solution of 5 micrograms/uL of soluble mouse protein in 100 mM Tris-HCL/6M urea, pH 8.0 buffer was added to a 1.5 mL siliconized Eppendorf tube, followed by the addition of 775 uL of MilliQ filtered water and 25 uL of 100 in M Tris-HCL, pH. 8 buffer. A 100 uL solution of 100 nanograms/uL of sequencing grade trypsin in 100 mM ammonium bicarbonate, pH 8.0 was added to the final concentration of 500 nanograms/uL of diluted soluble mouse protein and allowed to digest for 15 hours at 37° C. The pH of the soluble mouse digest was lowered by adding 1 uL of formic acid in order to quench the trypsin digestion. The following solutions were then prepared: Solution A=12.5 femtomoles/uL of *E. coli* beta galactosidase, 2.5 femtomoles/uL of bovine serum albumin and 100 femtomoles/uL of the artificial protein trypsin digest, Solution B=125 nanograms/uL of soluble mouse digest with 12.5 femtomoles/uL of *E. coli* beta galactosidase, 2.5 femtomoles/uL of bovine serum albumin and 100 femtomoles/uL of the artificial peptide trypsin digest. 2 uL of solution A and solution B were injected separately on an LC/MS/MS system, with each containing an identical concentration of beta galactosidase, bovine serum albumin, and the artificial protein trypsin digest, onto a Eksigent Tempo 1D nano liquid chromatography system with an Acclaim PepMap100 (Dionex) 2 cm×75 uM $C_{18}$ trap column and an Acclaim PepMap100 (Dionex) 15 cm×75 uM $C_{15}$ analytical column. The trap column was washed for 4 minutes in 0.1% formic acid with a flow rate of 1 uL/minute. Following the trap wash, the valve was switched to the analytical column with a flow rate of 300 nL/minute and the following linear gradient: 5-35% acetonitrile from 0 minutes to 15 minutes, 35-80% acetonitrile from 15 minutes to 16 minutes, 80-80% acetonitrile from 16 minutes to 18 minutes, 80-5% acetonitrile from 18 minutes to 19 minutes, 5-5% acetonitrile from 19 minutes to 30 minutes. The nano HPLC eluent was continuously introduced into an Applied Biosystems 5600 Quadrupole-TOF mass spectrometer operating in the data-dependent positive ion mode. FIG. 10. shows the MS1 spectra of the doubly charged artificial peptide reporters in solution A, and FIG. 11. shows the same chromatogram zoomed in from 7-14 minutes. FIG. 12. shows the MS1 spectra of the triply charged artificial peptide reporters in solution A, and FIG. 13. shows the same chromatogram zoomed in from 7-14 minutes. FIG. 14. shows a chromatogram of solution A with a beta-galactosidase peptide (YSQQQLMETSHR) co-fractionating with an artificial peptide reporter (KPAAAAAAAAWR), and FIG. 15. shows the same chromatogram zoomed in from 7-11 minutes. FIG. 16. shows a chromatogram of Solution B with the same beta-galactosidase peptide (YSQQQLMETSHR) co-fractionating with an artificial peptide reporter (KPAAAAAAAAWR), and FIG. 17. shows the same chromatogram zoomed in from 7-11 minutes. The beta-galactosidase peptide (YSQQQLMETSHR) in solution A yielded an area of 2.301e5, whereas at an identical concentration in solution B it yielded an area of 3.985e5. The co-fractionating artificial peptide reporter (KPAAAAAAAAWR) yielded an area of 8.297e4 in solution A, whereas at an identical concentration in solution B it resulted in an area of 1.684e5. The areas for the beta-galactosidase peptide (YSQQQLMETSHR) increased 73.2% in solution B compared to solution A indicating an enhancement in the signal for the complex mixture. The beta-galactosidase area/co-fractionating artificial peptide reporter area yielded a ratio of 2.77 in solution A and 2.37 in solution B. Thus, by using the ratio of the beta-galactosidase/co-fractionating artificial peptide reporter in solution B compared to solution A 2.37/2.77=0.856×(25 femtomoles of beta-galactosidase)= 21.4 femtomoles of beta-galactosidase calculated in solution B which is in excellent agreement with the expected calculated value of 25 femtomoles of beta-galactosidase. The application of the present invention resulted in an error of 14%, whereas without using the present invention the concentration of beta-galactosidase would have been overestimated by 73%. Note that the relative positions of the beta-galactosidase peptide (YSQQQLMETSHR) and the co-fractionating artificial peptide reporter (KPAAAAAAAAWR) shift between the solution A and solution B LC/MS runs. These peaks co-fractionate to a greater degree in the solution B run as compared to the solution A run.

Figure 18:
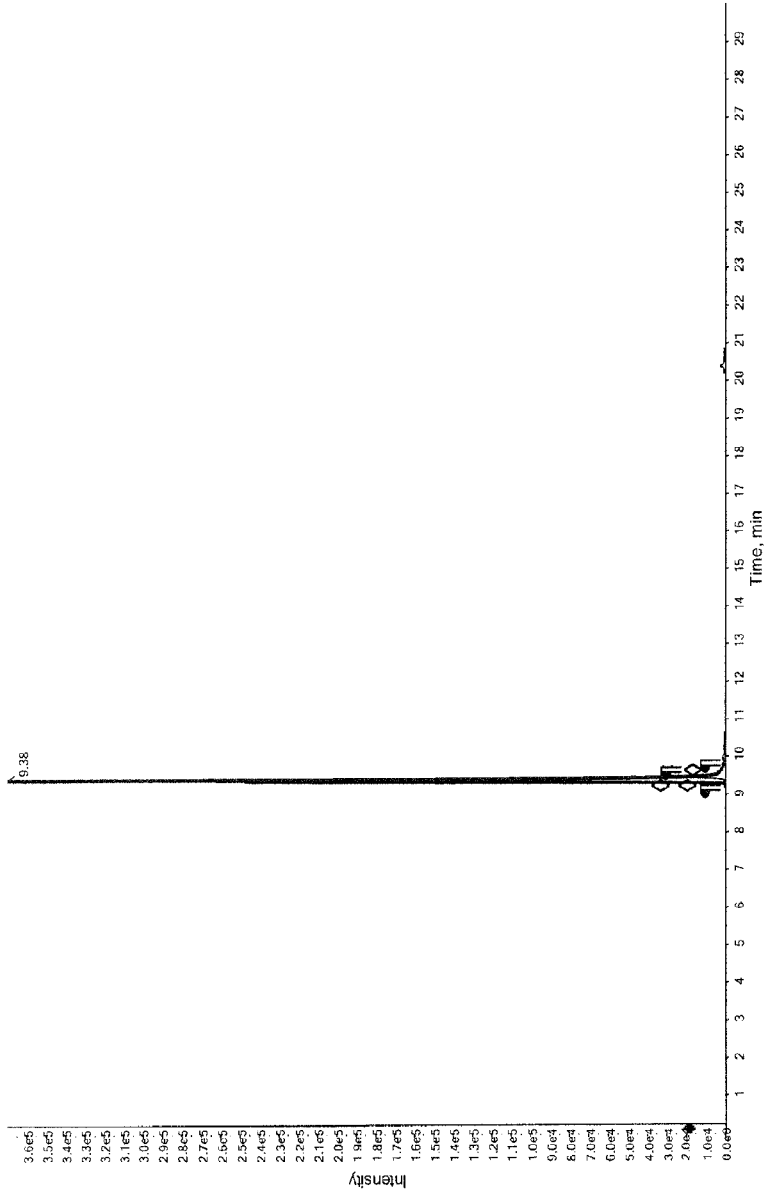
FIG. 18 shows an MS1 chromatogram of 395.2395 from the bovine serum albumin peptide LVTDLTK (blue trace) and the co-fractionating artificial peptide reporter KPAVAIFR doubly charged 451.2854 ion (orange trace) and triply charged 301.1921 ion (pink trace) in solution A (solution A as in FIG. 14)
Figure 19:
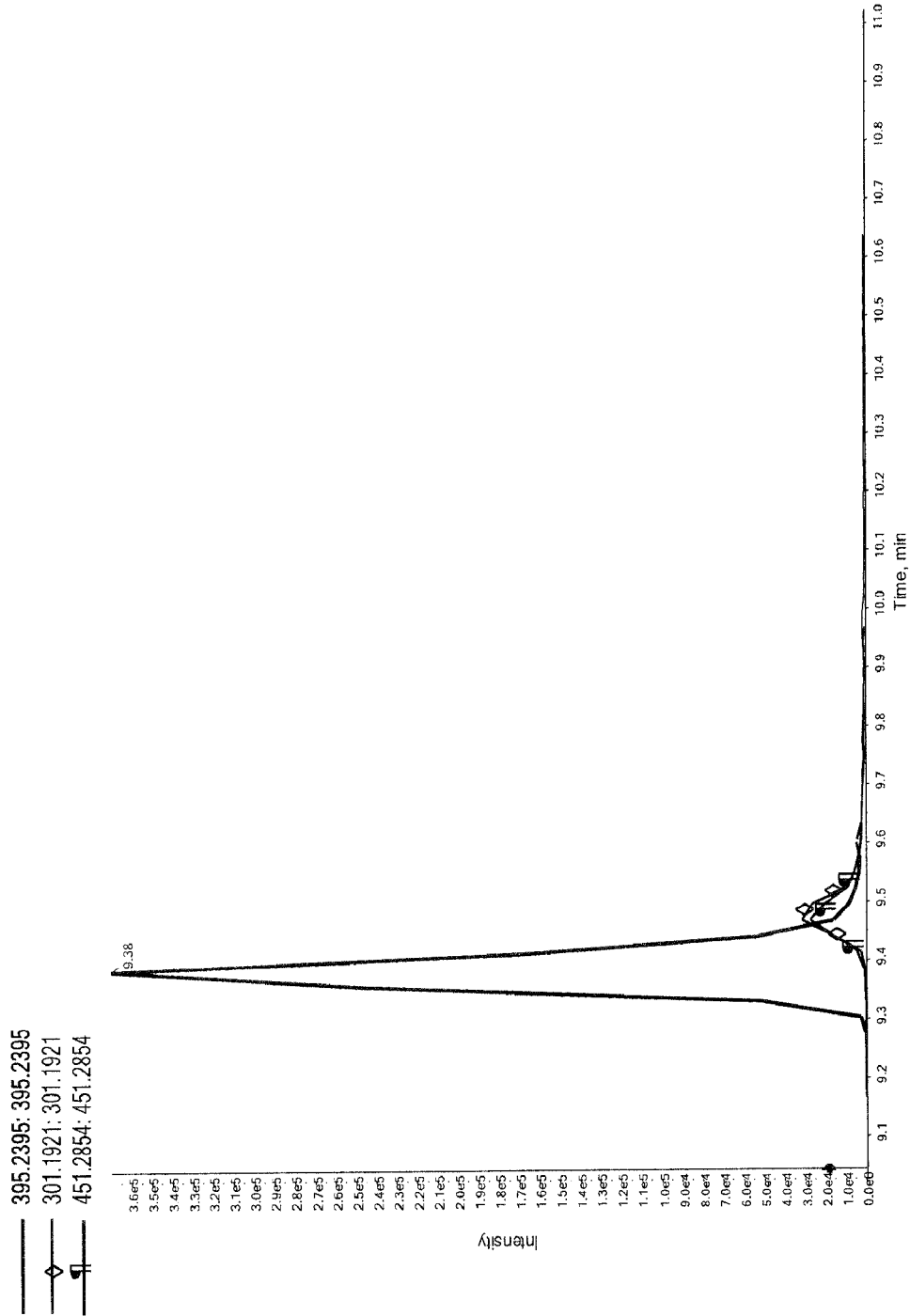
FIG. 19 shows the chromatogram of FIG. 18 in more detail.
Figure 20:
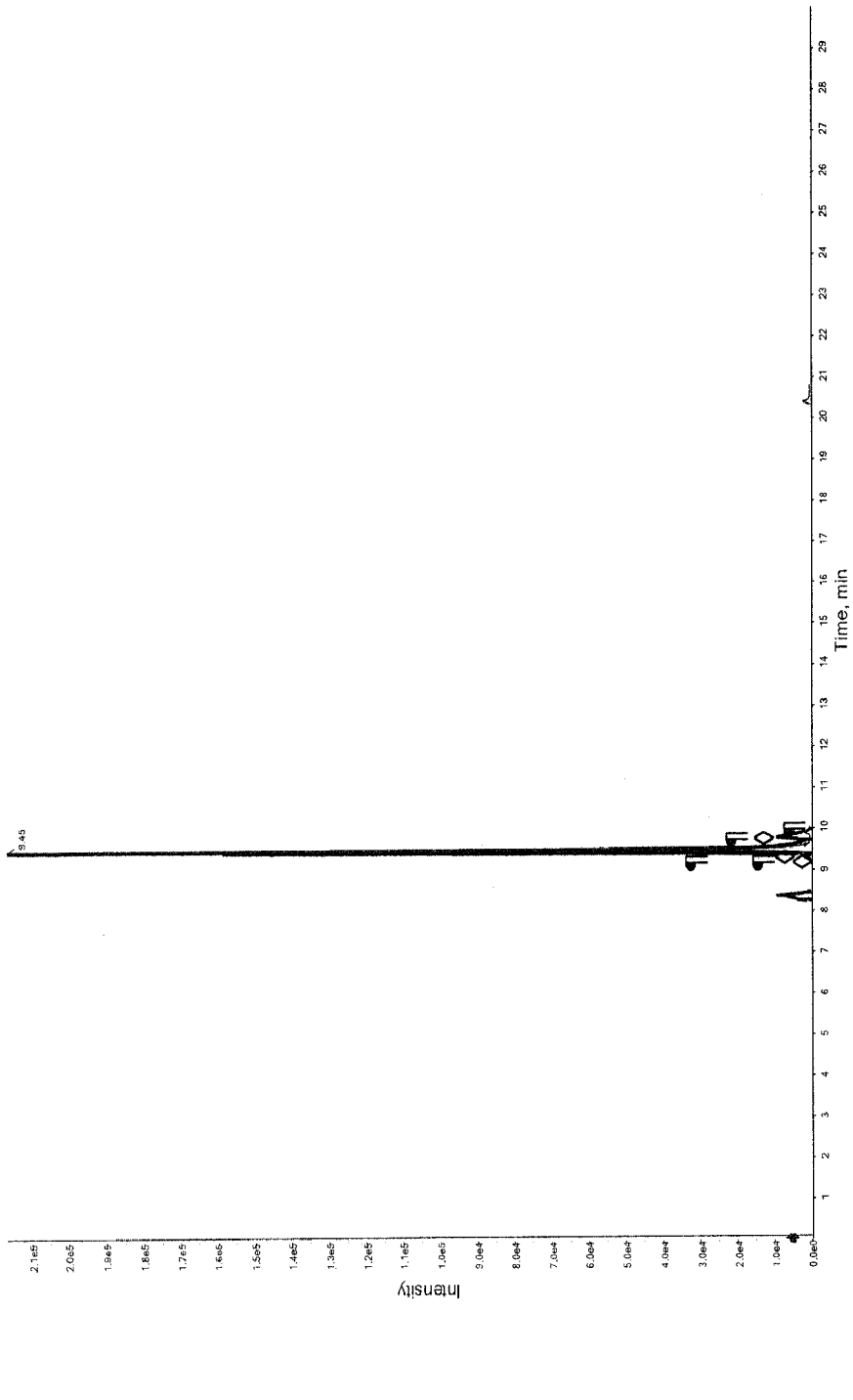
FIG. 20 show an MS1 chromatogram of 395.2395 from the bovine serum albumin peptide LVTDLTK (blue trace) and the co-fractionating artificial peptide reporter KPAVAIFR doubly charged 451.2854 ion (orange trace) and triply charged 301.1921 ion (pink trace) in solution B (solution B as in FIG. 16).
Figure 21:
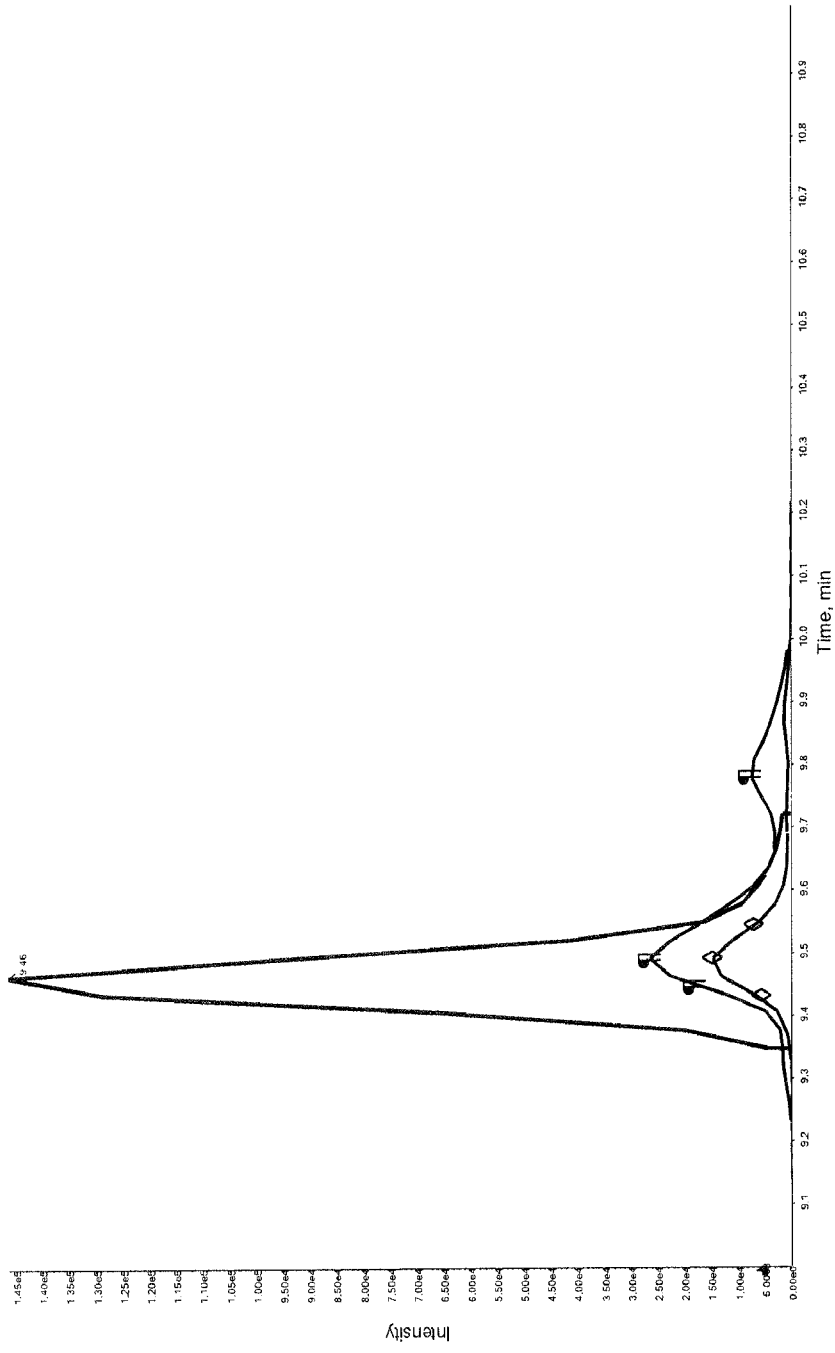
FIG. 21 shows the chromatogram of FIG. 20 in more detail.
Figure 22:
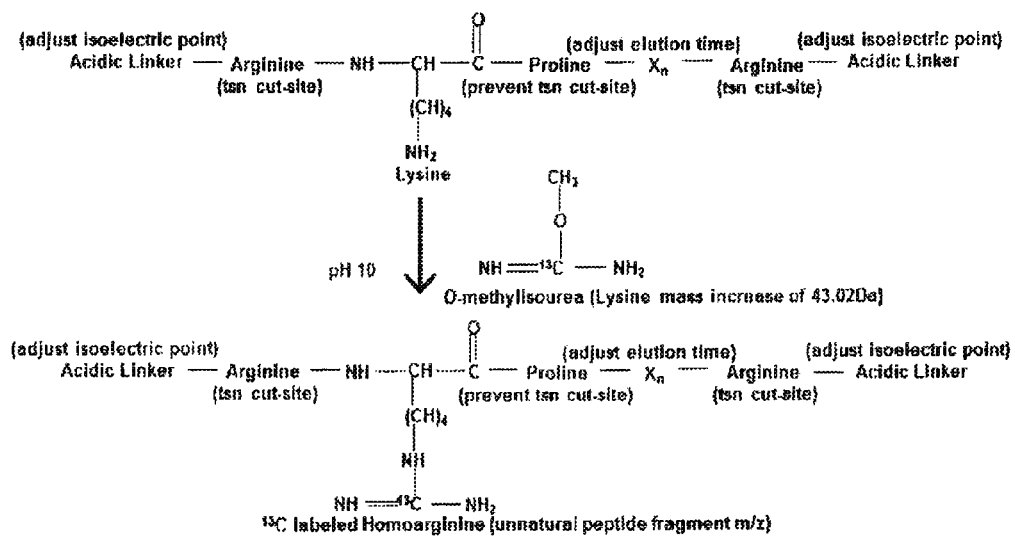
FIG. 22 shows the artificial protein guanidination reaction and overall features (tsn=trypsin, $X_n$=variable amino acid composition and length).
Figure 23:
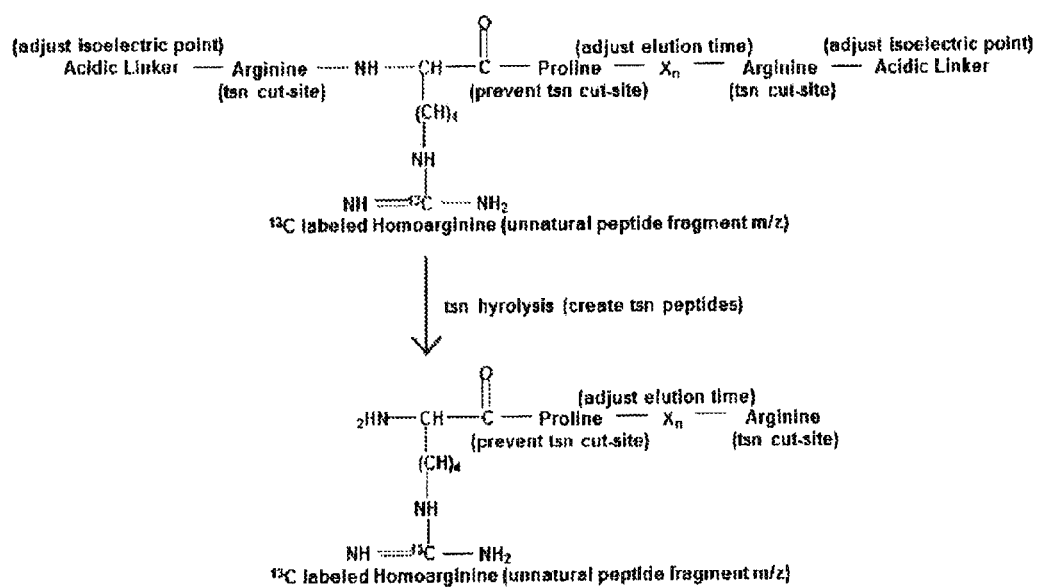
FIG. 23 shows the trypsin hydrolysis of artificial protein (tsn=trypsin, Xn=variable amino acid composition and length).
Figure 24:
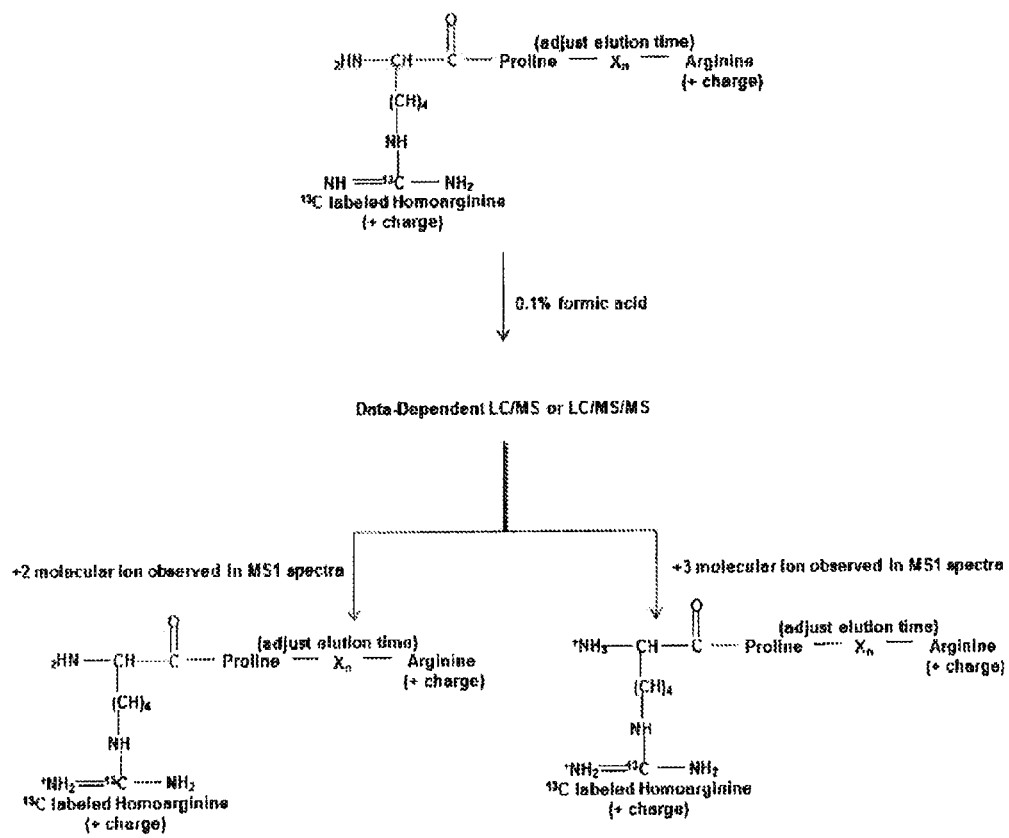
FIG. 24 illustrates the use of +2 and +3 molecular ions from artificial peptide MS1 spectra ($X_n$=variable amino acid composition and length).
Figure 25:
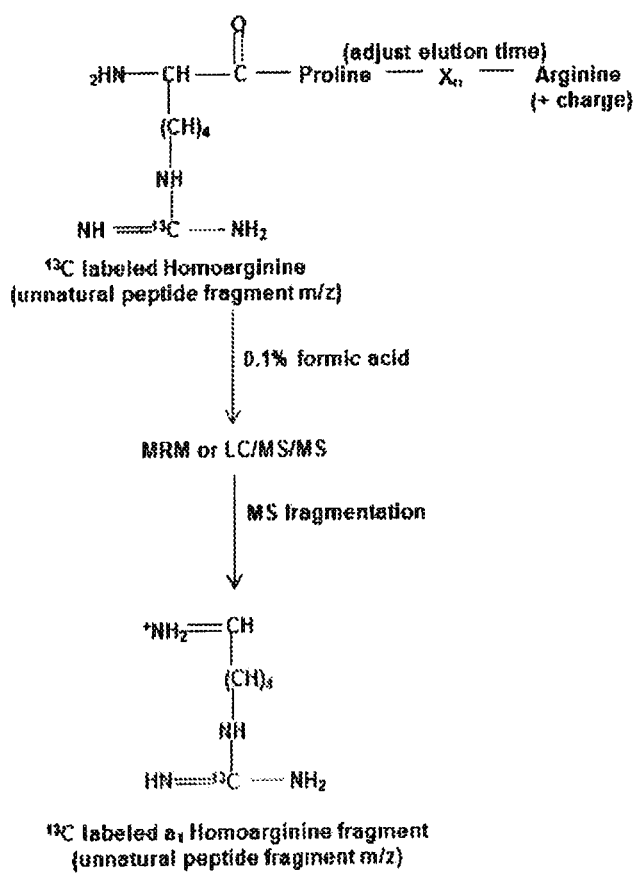
FIG. 25 shows the artificial peptide unnatural peptide ink fragment ion (Xn=variable amino acid composition and length).

In addition, the absolute concentration of the bovine serum albumin peptide (LVTDLTK) was also quantified using the doubly and triply charged co-fractionating artificial peptide reporter (KPAVAIFR). The MS1 chromatogram of (LVTDLTK) and the doubly and triply charged forms of (KPAVAIFR) in solution A are shown in FIG. 18, and a zoomed in chromatogram is shown in FIG. 19. The solution B MS1 peaks for (LVTDLTK) and the doubly and triply charged forms of (KPAVAIFR) are shown in FIG. 20 and a zoomed in chromatogram is shown in FIG. 21. The ratio of the doubly and triply charged forms of the artificial peptide (KPAVAIFR) should remain constant in solution A and solution B in the event that no m/z interference is occurring as a result of similar co-eluting m/z mouse analytes in solution B. However, the ratio of the doubly charged monoisotopic (KPAVAIFR) molecular ion 451.2854 peak area to the triply charged monoisotopic (KPAVAIFR) molecular ion 301.1921 peak area in solution A=1.476e5/1.785e5=0.826, whereas in solution B the ratio=1.953e5/1.033e5=1.890. The change in the ratio between solution A and solution B indicates that m/z interference is occurring in the artificial peptide reporter (KPAVAIFR) in solution B. In instances where interference is detected, the peak area for the artificial peptide reporter that has either the greatest decrease or smallest increase in the solution with a complex mixture (solution B) as compared to a solution containing a known amount of pure standards and the artificial peptide reporters (solution A) will be used to normalize for mass spectrometry detection efficiency. Therefore, the triply charged molecular ion of (KPAVAIFR) which had the greatest decrease in solution B as compared to solution A will be used to normalize for mass spectrometry detection efficiency. A comparison of the ratio of 2.5 femtomoles/uL of bovine serum albumin to 100 femtomoles/uL of the artificial peptide reporters in solution A containing the artificial peptide reporters, beta-galactosidase, and bovine serum albumin in 0.1% formic acid to solution B containing an identical concentration of the artificial peptide reporters, beta-galactosidase, bovine serum albumin, and 125 nanograms/uL of soluble mouse digest. The peak area obtained for the bovine serum albumin peptide (LVTDLTK) divided by the peak area obtained for the triply charged co-fractionating artificial peptide (KPAVAIFR) in solution A=1.536e6/ 1.785e5=8.605. The ratio of 8.605 is the value obtained when 2.5 femtomoles/uL of BSA is present in a solution containing 100 femtomoles/uL of the artificial peptide reporters and can be used to determine the concentration of the bovine serum albumin peptide (LVTDLTK). In solution B with an identical concentration of bovine serum albumin and the artificial peptide reporters in the presence of 250 nanograms/uL of soluble mouse digest the peak area obtained for the bovine serum albumin peptide (LVTDLTK) divided by the peak area obtained for the co-fractionating triply charged artificial peptide (KPAVAIFR)=8.663e5/1.033e5=8.386. Since the ratio value for 2.5 femtomoles/uL of bovine serum albumin peptide (LVTDLTK) in solution A containing standard solutions of bovine serum albumin and beta-galactosidase in the presence of the artificial peptide reporters by adding an identical amount of the artificial peptide reporters in solution B with the soluble mouse digest the absolute concentration of bovine serum albumin in solution B can be determined by the equation: (ratio of (LVTDLTK) to (KPAVAIFR) in solution A)/ (2.5 femtomoles/uL)=(ratio of (LVTDLTK) to (KPAVAIFR) in solution B)/(unknown concentration of bovine serum albumin). Solving the equation for the unknown concentration of bovine serum albumin peptide (LVTDLTK) in solution B=(2.5 femtomoles/uL×8.386)/(8.605)=2.436 femtomoles/ uL of bovine serum albumin peptide (LVTDLTK) in solution B. This value is within 2.6% of the correct theoretical value of 2.5 femtomoles/uL of bovine serum albumin. The peak area value for (LVTDLTK) decreased by 44% in solution B compared to solution A, and thus without using the artificial peptide reporter the concentration of the bovine serum albumin peptide (LVTDLTK) in solution B would incorrectly be determined as 1.4 femtomoles/uL.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. These patents and publications, including each of those mentioned in the reference list, are incorporated herein by reference to the same extent as if each individual application or publication was specifically and individually incorporated herein by reference, and to the same extend as if each were explicitly written herein including figures.

The foregoing description is illustrative of particular embodiments of the invention, but is not meant to be a limitation upon the practice thereof. The following claims, including all equivalents thereof, are intended to define the scope of the invention.

What is claimed:

1. A method for characterizing an analyte in a sample, said methods comprising:
   (a) combining a plurality of reporters with the sample containing the analyte to create a mixture, wherein each reporter generates a distinct reporter peak, the plurality of reporters provide a continuous set of reporter peaks during at least a fraction of the elution range of the sample and the plurality of reporters are not present in the sample or are not predicted to be created from the sample during processing of the sample;
   (b) subjecting the mixture to fractionation by liquid chromatography to produce an eluate;
   (c) subjecting the eluate to detection by a mass spectrometric technique to generate a mass spectrometric signal from the analyte and at least one reporter co-eluting with the analyte; and
   (d) comparing the mass spectrometric signal from analyte to the mass spectrometric signal of at least one reporter co-eluting with the analyte.

2. The method of claim 1, wherein the comparing step involves generating a ratio of the mass spectrometric signal from the analyte to the mass spectrometric signal of at least one reporter co-eluting with the analyte.

3. The method of claim 1, wherein said method is used to normalize the levels of the analyte contained in different samples.

4. The method of claim 2, wherein an increase in the ratio indicates an increased concentration of the analyte in the sample and a decrease in the ratio indicates a decreased concentration of the analyte in the sample.

5. The method of claim 1, wherein the characterizing is quantifying a relative amount of the analyte.

6. The method of claim 1, wherein the characterizing is quantifying an absolute amount of the analyte.

7. The method of claim 1, wherein the plurality of reporters are a chemical reporter set.

8. The method of claim 1, wherein the plurality of reporters are a biological reporter set.

9. The method of claim 8, wherein the biological reporter set is a plurality of reporter peptides.

10. The method of claim 8, wherein the biological reporter set is an artificial protein, the artificial protein comprising a plurality of reporter peptides, each reporter peptide separated by a cleavable linker, wherein on cleavage of the cleavable linker the artificial protein generates the plurality of reporter peptides.

11. The method of claim 10, wherein the cleavable linker comprises a proteolytic digestion site, wherein on cleavage of the proteolytic digestion site the artificial protein generates a plurality of reporter peptides.

12. The method of claim 11, wherein the proteolytic digestion site is a target for an endoproteinase selected from the group consisting of trypsin, chymotrypsin, Lys-C, Glu-C, Asp-N proteinase K, V-8 protease, Arg-C or Pro-C.

13. The method of claim 10, wherein the amino acid sequence of the cleavable linker is designed to vary an isoelectric point of the artificial protein or mass of the artificial protein.

14. The method of claim 10, wherein the artificial protein comprises a repeating sequence of L1-[K/R—(X)n-K/R-L2] a, wherein L1 and L2 are each a cleavable linker which can be the same or different and L2 can vary for each repeating group, n is from 1 to 1000 and a is from 2 to 1000.

15. The method of claim 14, wherein the amino acid sequence of L1, L2 or both is designed to vary an isoelectric point of the artificial protein or mass of the artificial protein.

16. A method for characterizing an analyte in a sample, said methods comprising:
   (a). combining a plurality of peptide reporters with the sample containing the analyte to create a mixture wherein each reporter generates a distinct reporter peak, the plurality of reporters provide a continuous set of reporter peaks during at least a fraction of the elution range of the sample and the plurality of reporters are not present in the sample or are not predicted to be created from the sample during processing of the sample;
   (b) subjecting the mixture to fractionation by liquid chromatography to produce an eluate;
   (c) subjecting the eluate to detection by a mass spectrometric technique to generate a mass spectrometric signal from the analyte and at least one peptide reporter co-eluting with the analyte of interest; and
   (d) comparing the mass spectrometric signal from the analyte to the mass spectrometric signal of at least one reporter co-eluting with the analyte.

17. The method of claim 16, wherein the plurality of reporters are added to the sample prior to at least partial purification of the sample.

18. The method of claim 17 wherein the purifying is an electrophoretic purification using a gel matrix.

19. The method of claim 16, wherein the set of peptide reporters are generated from an artificial protein, the artificial protein comprising a plurality of reporter peptides, each reporter peptide separated by a cleavable linker, wherein on cleavage of the cleavable linker the artificial protein generates a plurality of reporter peptides.

20. The methods of claim 19, wherein the cleavable linker comprises a proteolytic digestion site, wherein on cleavage of the proteolytic digestion site the artificial protein generates the plurality of reporter peptides.

21. The methods of claim 20, wherein the proteolytic digestion site is a target for an endoproteinase selected from the group consisting of trypsin, chymotrypsin, Lys-C, Glu-C, Asp-N proteinase K, V-8 protease, Arg-C or Pro-C.

22. A reporter set for quantifying an analyte in a sample through mass spectrometry detection, said reporter set comprising a plurality of reporters, each reporter generating a distinct reporter peak wherein the plurality of reporters provide a continuous set of reporter peaks during at least a fraction of the elution range of the sample and the plurality of reporters are not present in the sample or are not predicted to be created from the sample during processing of the sample.

23. The reporter set of claim 22, wherein the reporter set is a chemical reporter set.

24. The reporter set of claim 22, wherein the reporter peptides are used to normalize for sample recovery, ion suppression, ion enhancement or a combination of the foregoing.

25. The reporter set of claim 22, wherein at least one of the reporter peptides co-elutes with the analyte.

26. The reporter set of claim 22, wherein the biological reporter set is an artificial protein, the artificial protein comprising a plurality of reporter peptides, each reporter peptide separated by a cleavable linker, wherein on cleavage of the cleavable linker the artificial protein generates a plurality of reporter peptides.

27. The reporter set of claim 26, wherein the cleavable linker comprises a proteolytic digestion site, wherein on cleavage of the proteolytic digestion site the artificial protein generates the plurality of reporter peptides.

28. The reporter set of claim 27, wherein the proteolytic digestion site is a target for an endoproteinase selected from the group consisting of trypsin, chymotrypsin, Lys-C, Glu-C, Asp-N proteinase K, V-8 protease, Arg-C or Pro-C.

29. The reporter set of claim 27, wherein the reporter peptides are used to normalize for sample recovery, ion suppression, ion enhancement or a combination of the foregoing.

30. The reporter set of claim 27, wherein at least one of the reporter peptides co-elutes with the analyte.

31. The method of claim 1, wherein the artificial protein and the analyte in the sample are subject to proteolytic degradation in the gel matrix.

* * * * *

```
SEQUENCE LISTING

<160> NUMBER OF SEQ ID NOS: 24

<210> SEQ ID NO 1
<211> LENGTH: 12
<212> TYPE: PRT
<213> ORGANISM: Escherichia coli

<400> SEQUENCE: 1

Tyr Ser Gln Gln Gln Leu Met Glu Thr Ser His Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Artificial peptide reporter

<400> SEQUENCE: 2

Lys Pro Ala Ala Ala Ala Ala Ala Ala Ala Trp Arg
1               5                   10

<210> SEQ ID NO 3
<211> LENGTH: 7
<212> TYPE: PRT
<213> ORGANISM: Bos taurus

<400> SEQUENCE: 3

Leu Val Thr Asp Leu Thr Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Artificial peptide reporter

<400> SEQUENCE: 4

Lys Pro Ala Val Ala Ile Phe Arg
1               5

<210> SEQ ID NO 5
<211> LENGTH: 10
<212> TYPE: PRT
<213> ORGANISM: Artificial sequence
<220> FEATURE:
<223> OTHER INFORMATION: Artificial peptide reporter
```

```
<400> SEQUENCE: 5

Lys Pro Ala Ala Ala Ala Ala Phe Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Artificial Peptide Reporter

<400> SEQUENCE: 6

Lys Pro Ala Ala Ala Ala Ala Ala Leu Arg
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Artificial Peptide Reporter

<400> SEQUENCE: 7

Lys Pro Ala Gly Val Ala Trp Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Artificial Peptide Reporter

<400> SEQUENCE: 8

Lys Pro Ala Ala Ala Ala Ala Ala Phe Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Artificial Peptide Reporter

<400> SEQUENCE: 9

Lys Pro Ala Ala Ala Ala Ala Ala Trp Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Artificial Peptide Reporter

<400> SEQUENCE: 10

Lys Pro Ala Ala Ala Ala Ala Ala Trp Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Artificial Peptide Reporter

<400> SEQUENCE: 11
```

Lys Pro Ala Ile Ile Ile Asn Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Artificial Peptide Reporter

<400> SEQUENCE: 12

Lys Pro Ala Ile Ile Ile Ala Arg
1               5

<210> SEQ ID NO 13
<211> LENGTH: 13
<212> TYPE: PRT
<213> ORGANISM: Artificial Sequence
<220> FEATURE:
<223> OTHER INFORMATION: Artificial Peptide Reporter

<400> SEQUENCE: 13

Lys Pro Ala Ala Ala Ala Ala Ala Ala Ala Ala Phe Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Artificial Peptide Reporter

<400> SEQUENCE: 14

Lys Pro Ala Ala Ala Ala Ala Ala Ala Ala Ala Trp Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Artificial Peptide Reporter

<400> SEQUENCE: 15

Lys Pro Ala Ala Ala Ala Ala Ala Ala Ala Ala Ala Trp Arg
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Artificial Peptide Reporter

<400> SEQUENCE: 16

Lys Pro Ala Gly Val Phe Val Val Arg
1               5

<210> SEQ ID NO 17
<211> LENGTH: 15
<212> TYPE: PRT
<213> ORGANISM: Artificial Sequence
<220> FEATURE:
<223> OTHER INFORMATION: Artificial Peptide Reporter

<400> SEQUENCE: 17

Lys Pro Ala Ala Ala Ala Ala Ala Ala Ala Ala Ala Ala Trp Arg
1               5                   10                  15

```
<210> SEQ ID NO 18
<211> LENGTH: 8
<212> TYPE: PRT
<213> ORGANISM: Artificial Sequence
<220> FEATURE:
<223> OTHER INFORMATION: Artificial Peptide Reporter

<400> SEQUENCE: 18

Lys Pro Ala Ile Ile Ile Val Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Artificial Peptide Reporter

<400> SEQUENCE: 19

Lys Pro Ala Ile Ile Ile Ile His Arg
1               5

<210> SEQ ID NO 20
<211> LENGTH: 11
<212> TYPE: PRT
<213> ORGANISM: Artificial Sequence
<220> FEATURE:
<223> OTHER INFORMATION: Artificial Peptide Reporter

<400> SEQUENCE: 20

Lys Pro Ala Gly Val Ala Trp Val Ala Val Arg
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Artificial Peptide Reporter

<400> SEQUENCE: 21

Lys Pro Ala Ile Ile Ile Ile Gly Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Artificial Peptide Reporter

<400> SEQUENCE: 22

Lys Pro Ala Ile Ile Ile Ile Arg
1               5

<210> SEQ ID NO 23
<211> LENGTH: 894
<212> TYPE: DNA
<213> ORGANISM: Artificial sequence
<220> FEATURE:
<223> OTHER INFORMATION: Assembly of reporter peptides

<400> SEQUENCE: 23
catatggaag aagaacgtaa accggcggcg gcggctgcgg ctttccgtga agaagaacgt      60
aaaccggcgg cggcggcggc ggcggcactg cgtgacgaag atcgtaaacc ggcaggtgtc     120
```

-continued

```
gcatggcgtg atgacgatcg caagcctgcg gcggcggcgg cggcggcatt tcgtgacgat    180
gaacgcaagc cgcggcggc ggcggcggca tggcgtgaag atgaacgcaa gccagcggcg    240
gcggcggcgg cggcatggag agaagacgat cgcaaaccgg cgattatcat taaccgtgaa    300
gaagaacgca aaccggcgat cattatcgcc cgtgaagatg accgcaagcc ggcggcggcg    360
gcggcggcgg cggcggcatt ccgtgaagcg gatgaccgca aacctgcggc ggcggcggcg    420
gcggcggcat ggagggaaga tgaacgcaaa cccgcggcgg cggcggcggc ggcggcggca    480
tggagggacg atgaccgcaa accggccgtg gcaatctttc gtgatgatga ccgcaaacca    540
gcggcggcgc cggcggcggc ggcggcggca tggagggatg aagatcgcaa accggcgggc    600
gttttcgtgg ttcgtgacga agaccgtaag cctgcggcgg cggcggcggc ggcggcggcg    660
gcggcatgga gggaagaaga tgccgtaaa ccggccatta tcattgttcg tgaagatgaa    720
cgcaaaccgg ccatcattat cattcatcgc gaagaagaac gcaagcctgc aggtgtcgca    780
tgggtcgcag tgcgtgatga agatcgcaaa ccggcgatta tcatcattgg tcgtgaagaa    840
cgcaaaccgg ctattattat catccgtgtt ctcgagcacc accaccacca ccac    894
```

<210> SEQ ID NO 24
<211> LENGTH: 297
<212> TYPE: PRT
<213> ORGANISM: Artificial sequence
<220> FEATURE:
<223> OTHER INFORMATION: Assembly of reporter peptides

<400> SEQUENCE: 24

```
Met Glu Glu Arg Lys Pro Ala Ala Ala Ala Ala Ala Phe Arg Glu
1               5                   10                  15

Glu Glu Arg Lys Pro Ala Ala Ala Ala Ala Ala Leu Arg Asp Glu
                20                  25                  30

Asp Arg Lys Pro Ala Gly Val Ala Trp Arg Asp Asp Arg Lys Pro
            35                  40                  45

Ala Ala Ala Ala Ala Ala Ala Phe Arg Asp Asp Glu Arg Lys Pro Ala
    50                  55                  60

Ala Ala Ala Ala Trp Arg Glu Asp Glu Arg Lys Pro Ala Ala Ala
65                  70                  75                  80

Ala Ala Ala Trp Arg Glu Asp Asp Arg Lys Pro Ala Ile Ile Ile
                85                  90                  95

Asn Arg Glu Glu Glu Arg Lys Pro Ala Ile Ile Ile Ala Arg Glu Asp
                100                 105                 110

Asp Arg Lys Pro Ala Ala Ala Ala Ala Ala Ala Ala Phe Arg Glu
            115                 120                 125

Ala Asp Asp Arg Lys Pro Ala Ala Ala Ala Ala Ala Ala Ala Trp Arg
    130                 135                 140

Glu Asp Glu Arg Lys Pro Ala Ala Ala Ala Ala Ala Ala Ala Trp
145                 150                 155                 160

Arg Asp Asp Asp Arg Lys Pro Ala Val Ala Ile Phe Arg Asp Asp
                165                 170                 175

Arg Lys Pro Ala Ala Ala Ala Ala Ala Ala Ala Trp Arg Asp
            180                 185                 190

Glu Asp Arg Lys Pro Ala Gly Val Phe Val Val Arg Asp Glu Asp Arg
    195                 200                 205

Lys Pro Ala Ala Ala Ala Ala Ala Ala Ala Trp Arg Glu
            210                 215                 220

Glu Glu Cys Arg Lys Pro Ala Ile Ile Ile Val Arg Glu Asp Glu Arg
225                 230                 235                 240
```

-continued

```
Lys Pro Ala Ile Ile Ile Ile His Arg Glu Glu Glu Arg Lys Pro Ala
            245             250                 255

Gly Val Ala Trp Val Ala Val Arg Asp Glu Asp Arg Lys Pro Ala Ile
            260             265                 270

Ile Ile Ile Gly Arg Glu Glu Arg Lys Pro Ala Ile Ile Ile Ile Arg
            275             280                 285

Val Leu Glu His His His His His His
        290             295
```